(12) United States Patent
Cheng et al.

(10) Patent No.: US 11,951,187 B2
(45) Date of Patent: Apr. 9, 2024

(54) NIR-II IMAGING PROBE AND METHODS OF USING THE NIR-II IMAGING PROBE FOR DYNAMIC IN VIVO TRACKING

(71) Applicant: The Board of Trustees of the Leland Stanford Junior University, Stanford, CA (US)

(72) Inventors: Zhen Cheng, Mountain View, CA (US); Hao Chen, Menlo Park, CA (US)

(73) Assignee: The Board of Trustees of Leland Stanford Junior University, Stanford, CA (US)

( * ) Notice: Subject to any disclaimer, the term of this patent is extended or adjusted under 35 U.S.C. 154(b) by 268 days.

(21) Appl. No.: 17/179,948

(22) Filed: Feb. 19, 2021

(65) Prior Publication Data

US 2021/0252167 A1   Aug. 19, 2021

Related U.S. Application Data

(60) Provisional application No. 62/978,405, filed on Feb. 19, 2020.

(51) Int. Cl.
*A61K 49/00* (2006.01)

(52) U.S. Cl.
CPC ...... *A61K 49/0056* (2013.01); *A61K 49/0021* (2013.01); *A61K 49/0097* (2013.01)

(58) Field of Classification Search
None
See application file for complete search history.

(56) References Cited

FOREIGN PATENT DOCUMENTS

WO   WO-2016133462 A1 * 8/2016 ......... A61K 49/0093

OTHER PUBLICATIONS

Look et al. Ligand-Modified Human Serum Albumin Nanoparticles for Enhanced Gene Delivery. 2015 Mol. Pharm. 12: 3202-3213. (Year: 2015).*
Antaris et al. A high quantum yield molecule-protein complex fluorophore for near-infrared II imaging. 2017 Nat. Commun. 8:15269, 11 p. (Year: 2017).*
Chen et al. In vivo real-time visualization of mesenchymal stem cells tropism for cutaneous regeneration using NIR-II fluorescence imaging. 2015 Biomaterials 53: 265-273. (Year: 2015).*

* cited by examiner

*Primary Examiner* — Jennifer Chin
(74) *Attorney, Agent, or Firm* — Thomas | Horstemeyer, LLP

(57) ABSTRACT

The disclosure provides NIR-II imaging probes and methods of using the NIR-II imaging probes for dynamic in vivo tracking of cells, such as stem cells, or other substances. NIR-II imaging probes can include a biocompatible NIR-II dye molecule coupled to an organic, biocompatible protein carrier complex, including a carrier protein coupled to a cell-penetrating peptide.

15 Claims, 26 Drawing Sheets

Specification includes a Sequence Listing.

FIG. 1G  FIG. 1H

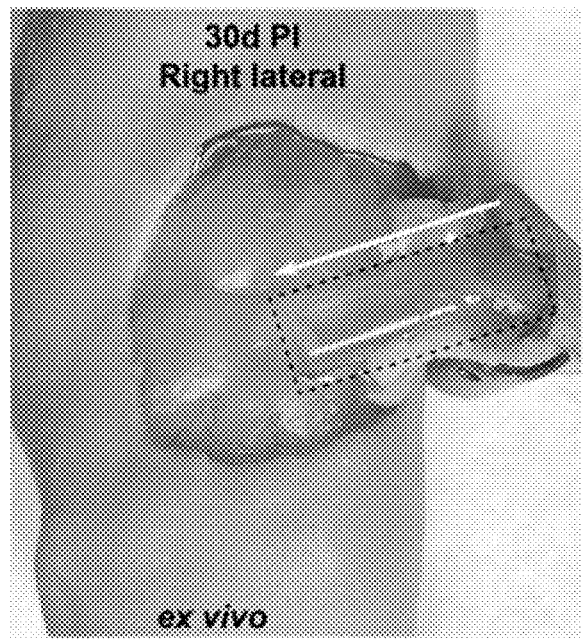
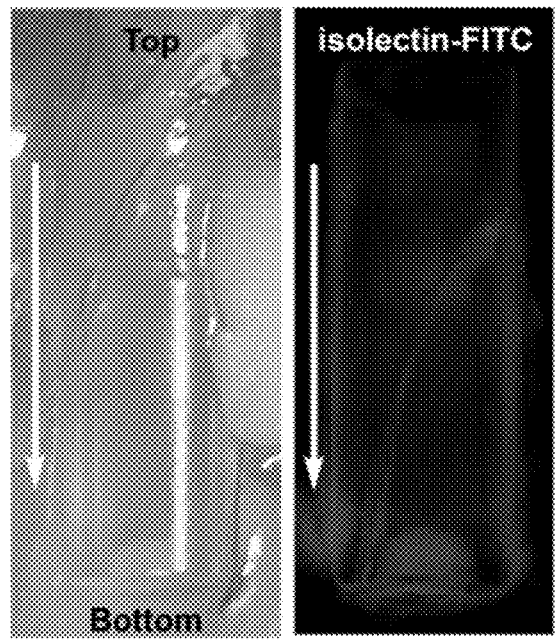
FIG. 2D　　FIG. 2E　　FIG. 2F
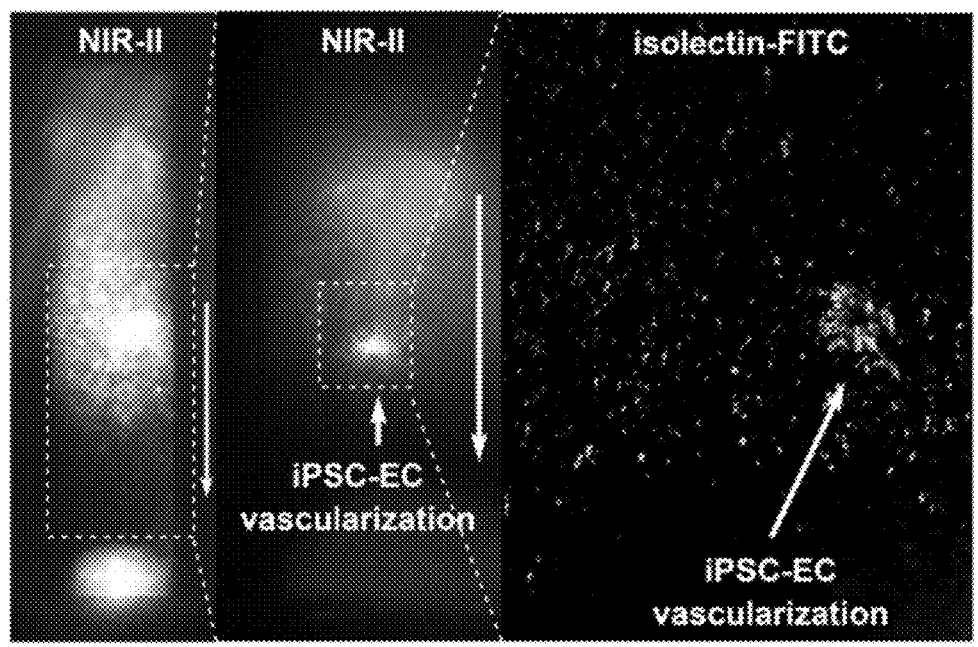
FIG. 2G　　FIG. 2H　　FIG. 2I

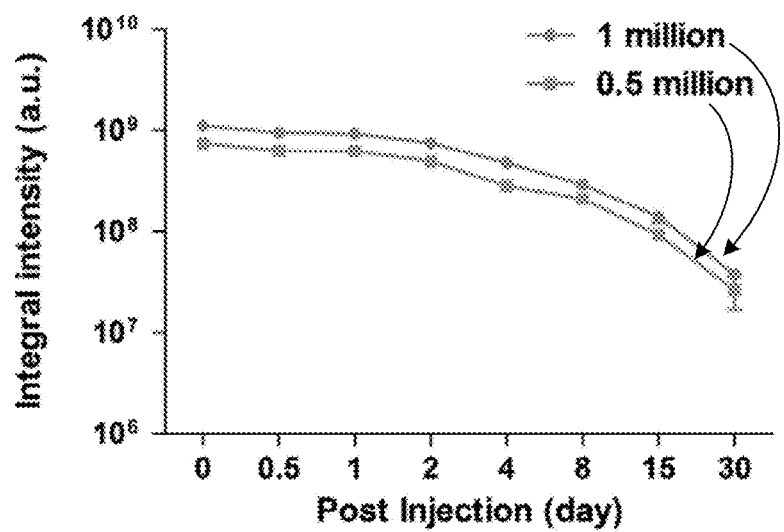
FIG. 2O
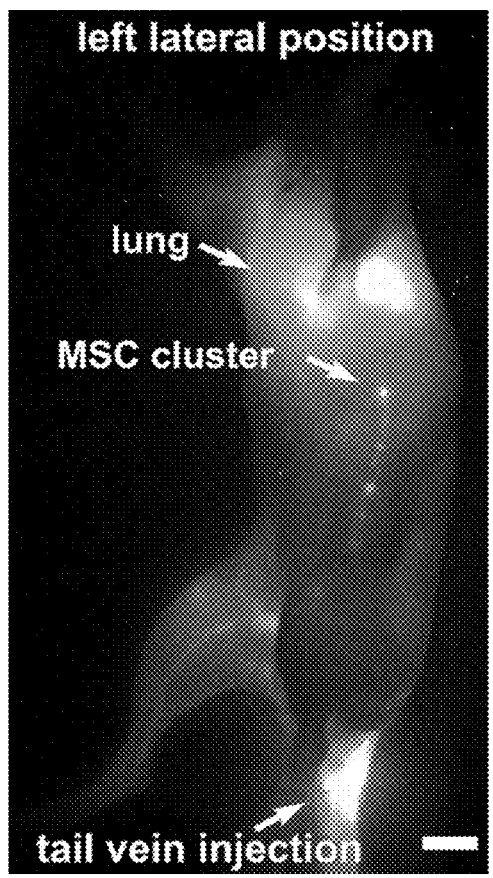 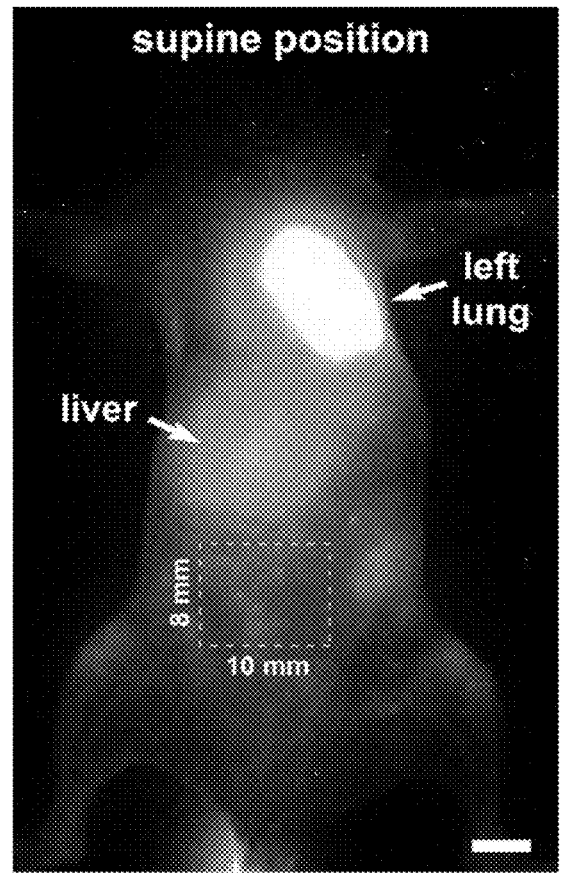
FIG. 3A  FIG. 3B

Mouse lung anatomy diagram

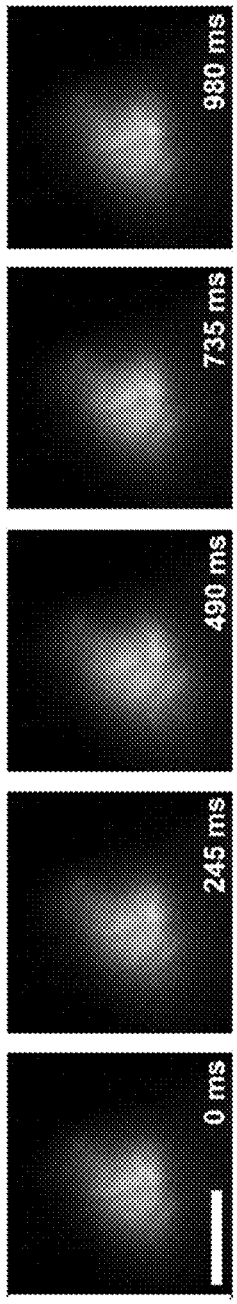
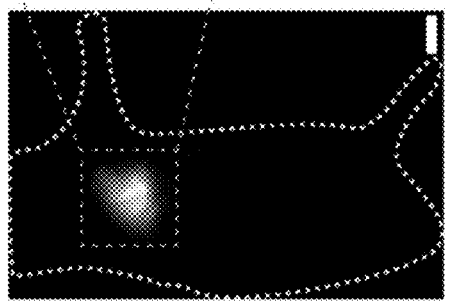
FIG. 3F
FIG. 3E
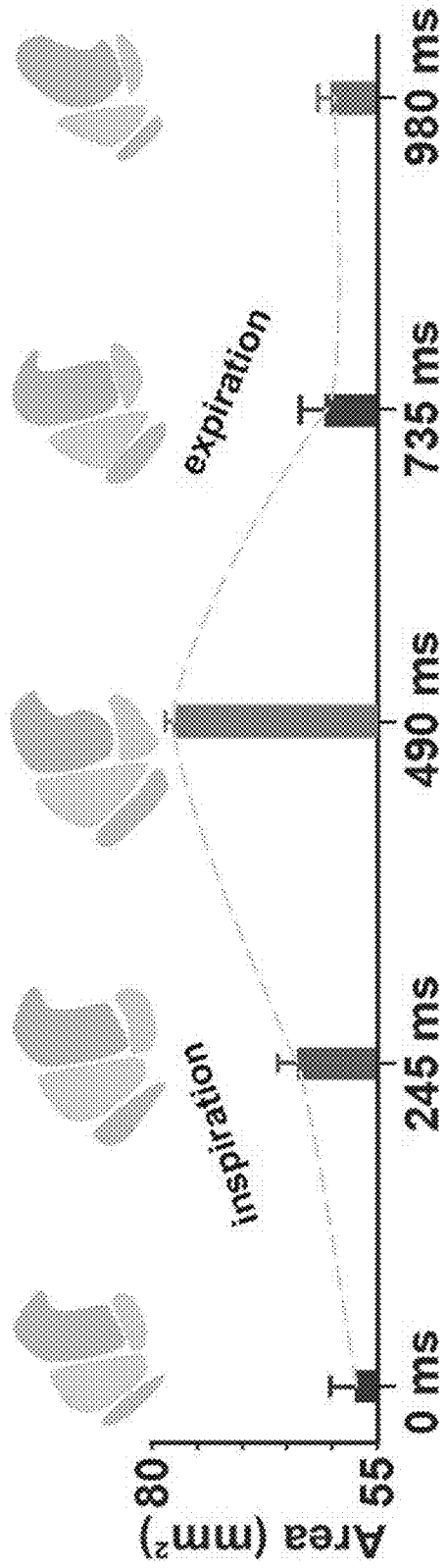
FIG. 3G

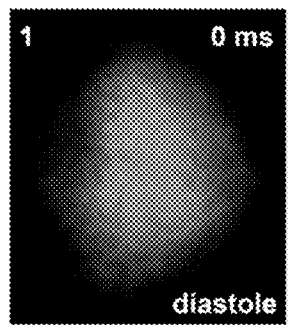
FIG. 3I
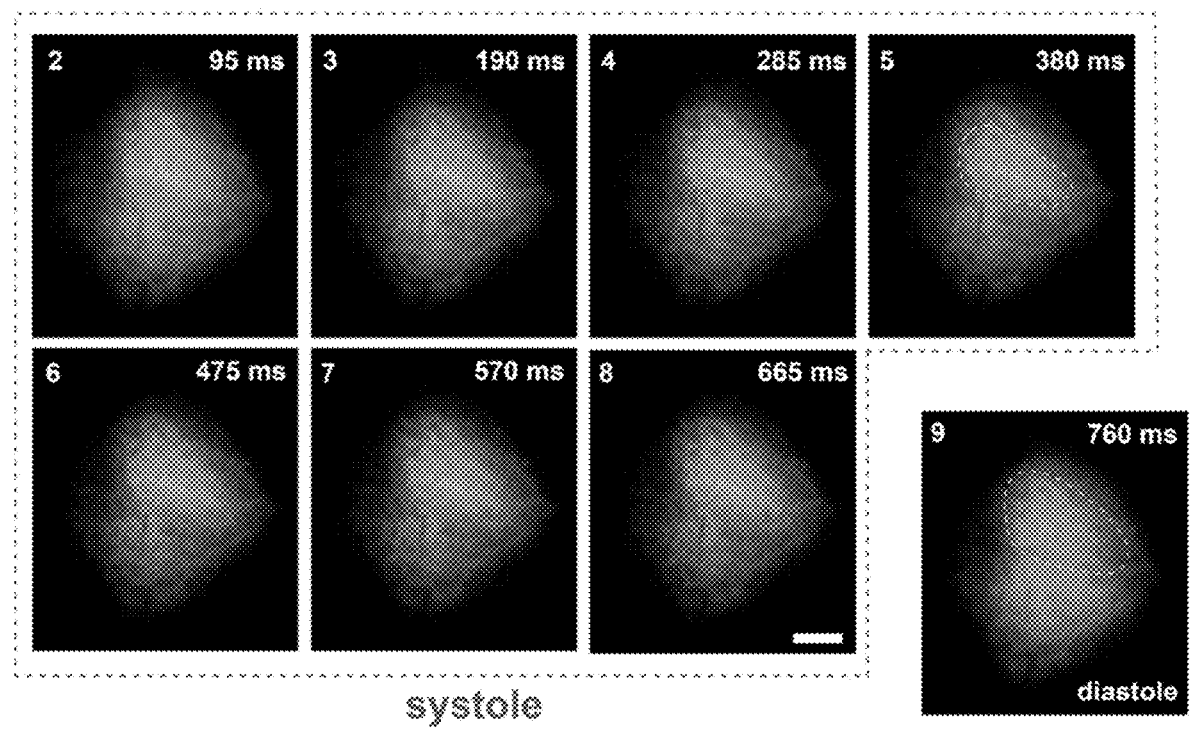
FIG. 3J  FIG. 3K

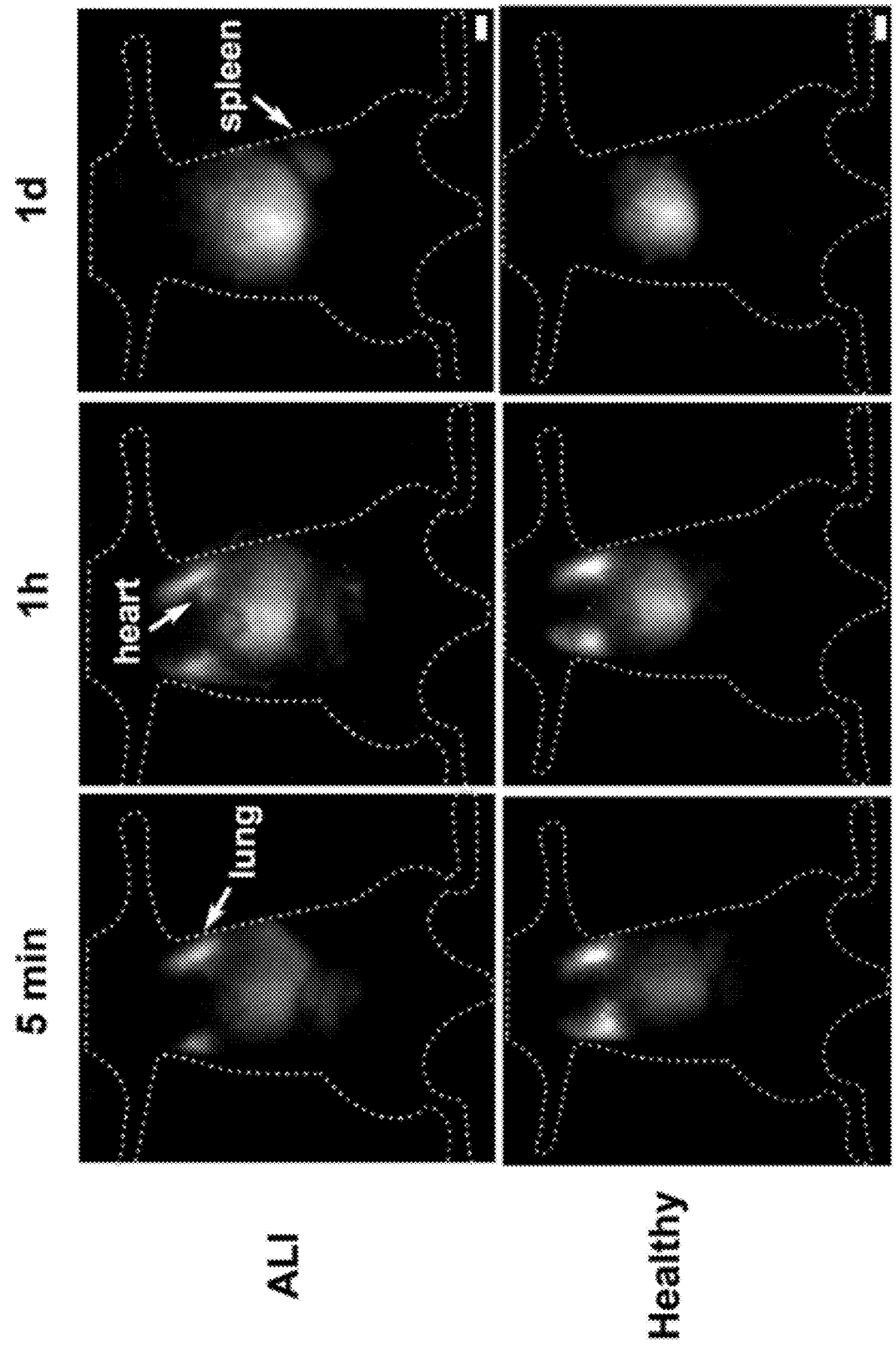

NIR-II IMAGING PROBE AND METHODS OF USING THE NIR-II IMAGING PROBE FOR DYNAMIC IN VIVO TRACKING

CROSS-REFERENCE TO RELATED APPLICATIONS

This application claims the benefit of and priority to U.S. Provisional Patent Application No. 62/978,405, filed on Feb. 19, 2020, entitled "NIR-II IMAGING PROBE AND METHODS OF USING THE NIR-II IMAGING PROBE FOR DYNAMIC IN VIVO TRACKING," the contents of which is incorporated by reference herein in its entirety.

SEQUENCE LISTING

This application contains a sequence listing filed in electronic form as an ASCII.txt file entitled 221907-1345_ST25.K created on Feb. 18, 2020 and having a size of 1 KB. The content of the sequence listing is incorporated herein in its entirety.

BACKGROUND

Optical imaging probes have been studied for in vivo imaging and tracking of various biologics, such as cells (including stem cells, immune cells, cancer cells, donor cells, etc.), tissues, small molecule therapeutics, biomolecules (peptides, nucleotides, etc.), and the like. Cell therapy, including therapies using stem cells, immune cells, donor cells, and the like, is a promising approach for treatment of diseases, but it is difficult to track cells in vivo using optical imaging techniques.

Stem cell therapy holds high promises in regenerative medicine. A major challenge of clinical translation of stem cell therapy includes the ability to precisely and quantitatively evaluate the in vivo cell distribution, migration, and engraftment, which cannot be easily achieved by current techniques. For instance, magnetic resonance imaging, positron emission tomography/computed tomography, and conventional optical imaging encounter challenges, such as low resolution, radioactive risks, and limited tissue penetration depth.

SUMMARY

In various aspects described herein, imaging probes, pharmaceutical imaging compositions, imaging systems, methods of imaging tissues, and methods of making imaging probes are provided.

In some aspects described herein, the present disclosure provides NIR-II optical imaging probes, where the probes include: a biocompatible NIR-II dye molecule coupled to an organic, biocompatible protein carrier complex, where the protein carrier complex includes a carrier protein coupled to a cell-penetrating peptide (CPP), and where the probe emits detectable NIR-II fluorescence. The present disclosure also provides cells including a plurality or at least one NIR-II optical imaging probe of the present disclosure. In embodiments, the cells including the optical imaging probe(s) can be, but are not limited to, a stem cell, a pluripotent cell, an immune cell, a donor cell, and a cancer cell.

In other aspects, the present disclosure also provides pharmaceutically acceptable imaging compositions including a pharmaceutically acceptable carrier and a plurality of NIR-II optical imaging probes of the present disclosure or a plurality of target cells, a portion of which each include one or more of the NIR-II optical imaging probes of the present disclosure. The present disclosure also provides imaging kits including the pharmaceutically acceptable imaging composition of the present disclosure and instructions for administration of the pharmaceutically acceptable imaging composition to a patient and imaging of the patient.

Imaging methods are also provided in the present disclosure. According to aspects, methods of generating an image of a biological substance in an animal or human subject are provided. In embodiments, such methods can include the steps of administering to an animal or human subject a pharmaceutically acceptable composition including a plurality of the NIR-II optical imaging probes of the present disclosure, where the probe is adapted to target the biological substance of interest, and obtaining an image of the location of the NIR-II optical imaging probes in the animal or human subject by detecting and imaging the fluorescent signal.

According to additional aspects of the present disclosure, methods of in vivo imaging exogenous cells in a human or animal subject are provided. Such methods can include administering to an animal or human subject a pharmaceutically acceptable composition including a plurality of exogenous cells, where the exogenous cells contain one or more optical imaging probes, the optical imaging probes including a biocompatible NIR-II dye molecule coupled to an organic, biocompatible protein carrier complex, where the protein carrier complex including a carrier protein coupled to a cell-penetrating peptide (CPP), and where the probe emits detectable NIR-II fluorescence. The methods can further include obtaining an image of the location of the administered NIR-II optical imaging probes in a tissue of the animal or human subject by detecting and imaging the NIR-II fluorescence, where the location of the NIR-II optical imaging probe indicates the location of the exogenous cells.

Other systems, methods, features, and advantages of the coating compositions, coated articles, and methods of making thereof will be apparent to one with skill in the art upon examination of the following drawings and detailed description. It is intended that all such additional systems, methods, features, and advantages be included within this description, be within the scope of the present disclosure, and be protected by the accompanying claims.

BRIEF DESCRIPTION OF THE DRAWINGS

Further aspects of the present disclosure will be more readily appreciated upon review of the detailed description of its various embodiments, described below, when taken in conjunction with the accompanying drawings. The components in the drawings are not necessarily to scale, emphasis instead being placed upon clearly illustrating the principles of the present disclosure. Moreover, in the drawings, like reference numerals designate corresponding parts throughout the several views.

FIGS. 1A-1J illustrate synthesis of an NIR-II imaging probe of the present disclosure, referred to as "CelTrac1000" for long-term real-time cell tracking. (FIG. 1A) Chemical structure of CH-4T and preparation of the single molecule CelTrac1000 through integration with Tat-conjugated HSA. (FIG. 1B) Normalized UV-vis absorption and fluorescence spectra of CelTrac1000 in PBS (50 µM). (FIG. 1C) Plot of the maximum absorption and fluorescence intensities of CelTrac1000 at six different concentrations in PBS, indicating its linear response to concentration in a range of 0 to 50 µM. (FIG. 1D) Plot of the percentage of CelTrac1000 molecules in MSCs and iPSC-ECs under different treatments over 144 h. The cells were first incubated with 50 µM of CelTrac1000 in culture medium for 48 h, followed by incubation with probe-free culture medium until 96 h. LPS (10 µg/mL) was then added into the culture medium to continue the release test until 144 h. (FIG. 1E) NIR-II fluorescent microscope images (785 nm excitation, 1000LP, 1000 ms) of CelTrac1000-labelled iPSC-ECs cultured for 0, 7, 14, 21, 30 days and the labeled MSCs after 30 days. (FIGS. 1F, 1G) NIR-II fluorescent images (1000LP, 50 ms) and schematic illustration of CelTrac1000-labeled iPSC-ECs post subcutaneous injection at nine spots in a nude mouse. The cell numbers are 250,000, 125,000, 62,500, 31,250, 15,625, 7,812, 3,906, 1,953, and 976 at spots 1-9 accordingly. (FIG. 1H) Magnified NIR-II fluorescent images (1000LP, 100 ms) of the nine spots 30 days post injection. (FIG. 1I) Plot of the integral fluorescent intensities at spot 1 (250,000 iPSC-ECs) up to 30 days post injection. (FIG. 1J) Bright-field and NIR-II fluorescent microscope images (785 nm excitation, 1000LP, 1000 ms) of a skin section from spot 1 after 30 days post injection. The histological analysis of the skin section evaluated with immunofluorescent imaging of the ECs (CD144, red), injected iPSC-ECs (human mitochondria, green), and nuclei (DAPI, blue).

FIGS. 2A-2O illustrate directed in vivo angiogenesis assay for long-term evaluation of angiogenesis induced by iPSC-ECs. (FIG. 2A) A nude mouse implanted with two semi-closed silicone angioreactors in the left (1 million CelTrac1000-labeled iPSC-ECs) and right (0.5 million CelTrac100-labeled iPSC-ECs) lower back. (FIG. 2D) An immunofluorescent image of the iPSC-ECs after isolectin-FITC staining. (FIGS. 2E-2H) NIR-II fluorescent images (1000LP, 100 ms) of the extracted angioreactor from the left lower back, 30 days post transplantation. (FIG. 2I) Immunofluorescent microscopy image of iPSC-EC vascularization after isolectin-FITC staining. (FIG. 2O) Plot of the integral NIR-II fluorescent intensities of the angioreactors (1 and 0.5 million labeled iPSC-ECs, n=4) up to 30 days post injection.

FIGS. 3A-3L illustrate dynamic stem cell tracking in mouse circulation system. (FIG. 3A) Representative whole-body NIR-II fluorescent image (1100LP, 100 ms) of a mouse 5 mins post intravenous injection of CelTrac1000-labeled MSCs. Scale bar: 5 mm. (FIG. 3B-3C) The migration trajectory of MSC clusters in the circulatory system over 580 ms. The white outlined box (8×10 mm) of FIG. 3B is shown under high magnification over different time intervals in FIG. 3C. (FIG. 3D) Schematic illustration of mouse lung anatomy. The right lung has 4 lobes: superior, middle, inferior and post-caval lobes. The left lung has 1 lobe. (FIG. 3E) Representative NIR-II fluorescent image (1100LP, 200 ms) of mouse lung 1.5 h post intravenous injection of CelTrac1000-labeled MSCs. Scale bar: 5 mm. (FIG. 3F) The real-time monitoring of the lung lobe movement during inspiration and expiration over 980 ms. Scale bar: 5 mm. (FIG. 3G) The trend of total lung lobe area changes during inspiration and expiration processes. Data were extracted from (FIG. 3F) for analysis. (FIG. 3H) Schematic illustration of systole and diastole phases of the cardiac cycle. (I-K) NIR-II fluorescent image (1000LP, 50 ms) of heart in diastole and systole phases over 760 ms. Scale bar: 5 mm. (FIG. 3L) Quantitative analyses of the fluorescent areas of the heart in systole and diastole phases of the cardiac cycle, corresponding to FIGS. 3I-3K. Note, images in FIGS. 3A, 3B, 3F, and 3I-3K correspond to videos which, due to the format of this disclosure, could not be included, but are represented by the images and discussion provided herein.

FIGS. 4A-4H illustrate imaging and analysis of the biodistribution of MSCs in the mouse model of acute lung injury (ALI). (FIG. 4A) Representative NIR-II fluorescent images (1000LP, 100 ms) of the ALI mouse and healthy mouse upon intravenous injection of CelTrac1000-labeled MSCs (1 million), showing the distinct biodistribution signatures. Scale bar: 5 mm. (FIG. 4B) Quantitative analyses of the average fluorescent intensities from the organs (lung, heart, spleen, liver) at different times intervals (5 min, 1 h, 3 h, 6 h, 24 h, and 72 h post cell injection in the ALI and healthy mice, respectively. n=3, *p<0.05, p<0.01, *p<0.001, ****p<0.0001. (FIG. 4C) NIR-II fluorescent images (1000LP, 200 ms) of the whole lung, sectioned lung tissue (2 mm in thickness), and cryo-sectioned lung tissue (50 µm in thickness) from the ALI mouse. Scale bar: 5 mm. (FIG. 4D) H&E stained lung tissues from ALI and healthy mice. (FIG. 4E) NIR-II fluorescent images (1000LP, 200 ms) of the whole heart and cryo-sectioned heart tissue (50 µm in thickness) from the ALI mouse. Scale bar: 5 mm. (FIG. 4F) H&E stained heart tissues from ALI and healthy mice. (FIG. 4G) NIR-II fluorescent images (1000LP, 200 ms) of the whole spleen and cryo-sectioned spleen tissue (50 µm in thickness) from the ALI mouse. Scale bar: 5 mm. (FIG. 4H) H&E stained spleen tissues from ALI and healthy mice. The mice were sacrificed to collect organs 72 h post injection of the MSCs for ex vivo analyses.

(FIG. 5A) Representative NIR-II fluorescent images (1000LP, 100 ms) of the MI mice upon intravenous injection of CelTrac1000-labeled MSCs (2 million) and CelTrac1000 probe (0.2 µmol), respectively. Scale bar: 5 mm. Quantitative analyses of the average fluorescent intensities from heart (FIG. 5B), lung (FIG. 5C), and liver (FIG. 5D) at different time intervals (5 min, 1 h, 3 h, 6 h, 24 h, and 72 h) post injection of CelTrac1000-labeled MSCs and CelTrac1000 probes, respectively. n=3, *p<0.05, p<0.01, *p<0.001, ****p<0.0001. (FIG. 5E) NIR-II fluorescent image (1000LP, 200 ms) of the whole heart and cryo-sectioned heart tissue (50 µm in thickness) from the MI mouse injected with labeled cells. Scale bar: 2 mm. (FIG. 5F) Images of H&E stained heart tissues from the MI and healthy mice for comparison. The mice were sacrificed to collect organs 72 h post injection of the MSCs for ex vivo analyses.

(FIG. 6A) Representative NIR-II fluorescent images (1100LP, 200 ms) of a MCAO model mouse 5 min post intravenous injection of CelTrac1000-labeled MSCs (2 million). Note that the blood vessels in the left cerebral hemisphere of the stroke site are not visible while the right cerebral hemisphere can be clearly observed. Scale bar: 5 mm. (FIG. 6B) Representative NIR-II fluorescent images (1100LP, 200 ms) of the MCAO mouse at different time points (30 min, 1 h, 3 h, and 5 h) post intravenous injection of CelTrac1000-labeled MSCs. Scale bar: 5 mm. (FIG. 6C) Time course of fluorescence intensity in the brain blood vessels of a MCAO mouse corresponding to lines 1 and 2 in FIG. 6A and FIG. 6D) The cross-sectional NIR-II fluorescent intensity profiles of locations 1 and 2 in FIG. 6A. (FIG. 6E) Time course of fluorescence intensity in the brain of a MCAO mouse corresponding to the white dashed line in FIG. 6B, revealing the dynamic intensity changes in the left and right hemispheres.

DETAILED DESCRIPTION

Figure 1A:
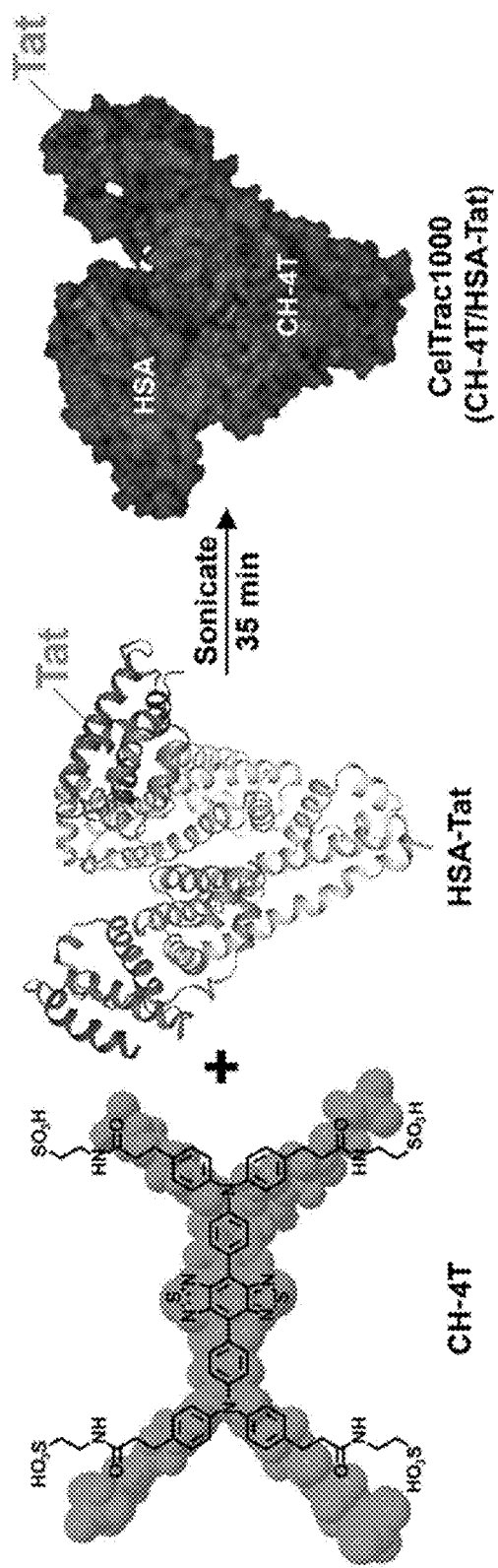

Before the present disclosure is described in greater detail, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit (unless the context clearly dictates otherwise), between the upper and lower limit of that range, and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, nanochemistry, organic chemistry, biochemistry, molecular biology, pharmacology, toxicology, and the like, which are within the skill of the art. Such techniques are explained fully in the literature.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20-25° C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only and is not intended to be limiting. It is also possible in the present disclosure that steps can be executed in different sequence where this is logically possible.

All publications and patents cited in this specification are cited to disclose and describe the methods and/or materials in connection with which the publications are cited. Publications and patents that are incorporated by reference, where noted, are incorporated by reference as if each individual publication or patent were specifically and individually indicated to be incorporated by reference. Such incorporation by reference is expressly limited to the methods and/or materials described in the cited publications and patents and does not extend to any lexicographical definitions from the cited publications and patents. Any lexicographical definition in the publications and patents cited that is not also expressly repeated in the instant application should not be treated as such and should not be read as defining any terms appearing in the accompanying claims. Any terms not specifically defined within the instant application, including terms of art, are interpreted as would be understood by one of ordinary skill in the relevant art; thus, is not intended for any such terms to be defined by a lexicographical definition in any cited art, whether or not incorporated by reference herein, including but not limited to, published patents and patent applications. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

It must be noted that, as used in the specification and the appended claims, the singular forms "a," "an," and "the" include plural referents unless the context clearly dictates otherwise. Thus, for example, reference to "a compound" includes a plurality of compounds. In this specification and in the claims that follow, reference will be made to a number of terms that shall be defined to have the following meanings unless a contrary intention is apparent.

As used herein, the following terms have the meanings ascribed to them unless specified otherwise. In this disclosure, "comprises," "comprising," "containing" and "having" and the like can have the meaning ascribed to them in U.S. patent law and can mean "includes," "including," and the like. In this disclosure, "consisting essentially of" or "consists essentially" or the like, when applied to methods and compositions encompassed by the present disclosure refers to compositions like those disclosed herein, but which may contain additional structural groups, composition components or method steps (or analogs or derivatives thereof as discussed above). Such additional structural groups, composition components or method steps, etc., however, do not materially affect the basic and novel characteristic(s) of the compositions or methods, compared to those of the corresponding compositions or methods disclosed herein. "Consisting essentially of" or "consists essentially" or the like, when applied to methods and compositions encompassed by the present disclosure have the meaning ascribed in U.S. Patent law and the term is open-ended, allowing for the presence of more than that which is recited so long as basic or novel characteristics of that which is recited is not changed by the presence of more than that which is recited, but excludes prior art embodiments.

Prior to describing the various embodiments, the following definitions are provided and should be used unless otherwise indicated.

Definitions

In describing and claiming the disclosed subject matter, the following terminology will be used in accordance with the definitions set forth below.

As used herein, "about," "approximately," and the like, when used in connection with a numerical variable, generally refers to the value of the variable and to all values of the variable that are within the experimental error (e.g., within the 95% confidence interval for the mean) or within +1-10% of the indicated value, whichever is greater.

As used herein, "active agent" or "active ingredient" refers to a substance, compound, or molecule, which is biologically active or otherwise, induces a biological or physiological effect on a subject to which it is administered to. In other words, "active agent" or "active ingredient" refers to a component or components of a composition to which the whole or part of the effect of the composition is attributed.

The term "pharmaceutically acceptable" describes a material that is not biologically or otherwise undesirable, i.e., without causing an unacceptable level of undesirable biological effects or interacting in a deleterious manner.

The term "pharmaceutically acceptable carrier" as used herein refers to a diluent, adjuvant, excipient, or vehicle with which a probe of the disclosure is administered and which is approved by a regulatory agency of the Federal or a state government or listed in the U.S. Pharmacopeia or other generally recognized pharmacopeia for use in animals, and more particularly in humans. Such pharmaceutical carriers can be liquids, such as water and oils, including those of petroleum, animal, vegetable or synthetic origin, such as peanut oil, soybean oil, mineral oil, sesame oil and the like. The pharmaceutical carriers can be saline, gum acacia, gelatin, starch paste, talc, keratin, colloidal silica, urea, and the like. When administered to a patient, the probe and pharmaceutically acceptable carriers can be sterile. Water is a useful carrier when the probe is administered intravenously. Saline solutions and aqueous dextrose and glycerol solutions can also be employed as liquid carriers, particularly for injectable solutions. Suitable pharmaceutical carriers also include excipients such as glucose, lactose, sucrose, glycerol monostearate, sodium chloride, glycerol, propylene, glycol, water, ethanol and the like. The present compositions, if desired, can also contain minor amounts of wetting or emulsifying agents, or pH buffering agents. The present compositions advantageously may take the form of solutions, emulsion, sustained-release formulations, or any other form suitable for use.

The term "nanoparticle" as used herein includes a nanoscale deposit of homogenous or heterogeneous material. Nanoparticles may be regular or irregular in shape and may be formed from a plurality of co-deposited particles that form a composite nanoscale particle. Nanoparticles may be generally spherical in shape or have a composite shape formed from a plurality of co-deposited generally spherical particles. Exemplary shapes for the nanoparticles include, but are not limited to, spherical, rod, elliptical, cylindrical, disc, and the like. In some embodiments, the nanoparticles have a substantially spherical shape. The term "nanoparticle" generally refers to a particle having a diameter of between about 1 and about 1000 nm. Similarly, by the term "nanoparticles" is meant a plurality of particles having an average diameter of between about 1 and about 1000 nm or about 1 to 500 nm or about 1 to 250 nm.

It will be understood by one of ordinary skill in the art that when referring to a population of nanoparticles as being of a particular "size", what is meant is that the population is made up of a distribution of sizes around the stated "size". Unless otherwise stated, the "size" used to describe a particular population of nanoparticles will be the mode of the size distribution (i.e., the peak size). By reference to the "size" of a nanoparticle is meant the length of the largest straight dimension of the nanoparticle. For example, the size of a perfectly spherical nanoparticle is its diameter.

The term "detectable" refers to the ability to detect a signal over the background signal. The detectable signal is defined as an amount sufficient to yield an acceptable image using equipment that is available for pre-clinical use. A detectable signal may be generated by one or more administrations of the probes of the present disclosure. The amount administered can vary according to factors such as the degree of susceptibility of the individual, the age, sex, and weight of the individual, idiosyncratic responses of the individual, the dosimetry, and the like. The amount administered can also vary according to instrument and digital processing related factors.

The term "in vivo imaging" as used herein refers to methods or processes in which the structural, functional, or physiological state of a living being is examinable without the need for a life-ending sacrifice.

The term "non-invasive in vivo imaging" as used herein refers to methods or processes in which the structural, functional, or physiological state of a being is examinable by remote physical probing without the need for breaching the physical integrity of the outer (skin) or inner (accessible orifices) surfaces of the body.

The term "detectable imaging moiety," "imaging probe," "detectable label" or "label" as used herein refers to an atom, or radioactive atom detectable by systems and methods such as, but not limited to, optical detection, γ-radiation detection, positron emission transmission, and the like. Some inorganic or organic molecules may be detected by an optical method, for example by fluorescence detection, light absorbance and the like. It should be noted that reference to detecting a signal from a probe also includes detecting a signal from a plurality of probes. In some embodiments, a signal may only be detected that is produced by a plurality of probes (e.g., nanoaggregates). Additional details regarding detecting signals (e.g., infared signals) are described below.

The "imaging probe" may be detected either externally to a subject human or non-human animal body or via use of detectors designed for use in vivo, such as intravascular radiation or optical detectors such as endoscopes, or radiation detectors designed for intra-operative use. The imaging moiety is preferably chosen from, the NIR-II fluorescent emitting probes of the present disclosure suitable for in vivo optical imaging. It is contemplated, however, that other detectable labels may also be incorporated into the probes of the disclosure including, but not limited to, a radioactive nuclide. When the imaging moiety is a radioactive metal ion, i.e. a radiometal, suitable radiometals can be either positron emitters such as $^{64}$Cu, $^{48}$V, $^{52}$Fe, $^{55}$Co, $^{94}$mTc or $^{68}$Ga or γ-emitters such as 99mTc, $^{111}$In, $^{113}$In, $^{67}$Ga. When the imaging moiety is a positron-emitting radioactive nonmetal, suitable such positron emitters can include: $^{11}$C, $^{13}$N, $^{15}$O, $^{17}$F, $^{18}$F, $^{75}$Br, $^{76}$Br, $^{76}$Br or $^{124}$I.

The term "biocompatible", as used herein, refers to a material that along with any metabolites or degradation products thereof that are generally non-toxic to the recipient and do not cause any significant adverse effects to the recipient and do not adversely affect the short-term viability or long-term proliferation of a target biological particle within a particular time range. Generally speaking, biocompatible materials are materials that do not elicit a significant inflammatory or immune response when administered to a patient.

The term "administration" refers to introducing an agent (or a compound including the agent, where the agent can be a NIR-II imaging probe of the present disclosure, for example) of the present disclosure into a subject. The preferred route of administration of the compounds is intravenous. However, any route of administration, such as oral, topical, subcutaneous, peritoneal, intraarterial, inhalation, vaginal, rectal, nasal, introduction into the cerebrospinal fluid, or instillation into body compartments can be used. In an embodiment, the agent is administered locally (e.g., colon) so that it is not systemically distributed throughout the body.

In accordance with the present disclosure, "a detectably effective amount" of the agent (e.g., an NIR-II imaging probe) of the present disclosure is defined as an amount sufficient to yield an acceptable image using equipment that is available for pre-clinical or clinical use. In an embodiment, a detectably effective amount of the agent of the present disclosure may be administered in more than one injection. The detectably effective amount of the agent of the present disclosure can vary according to factors such as the degree of susceptibility of the individual, the age, sex, and weight of the individual, idiosyncratic responses of the individual, the dosimetry, and the like. Detectably effective amounts of the agent of the present disclosure can also vary according to instrument and digital processing related factors. Optimization of such factors is well within the level of skill in the art.

As used herein, the term "subject" includes humans, mammals, and birds (e.g., mice, rats, pigs, cats, dogs, birds, and horses). Typical subjects to which compounds of the present disclosure may be administered will be mammals, particularly primates, especially humans. For veterinary applications, a wide variety of subjects will be suitable, e.g., livestock such as cattle, sheep, goats, cows, swine, and the like; poultry such as chickens, ducks, geese, turkeys, and the like; and domesticated animals particularly pets such as dogs and cats. For diagnostic or research applications, a wide variety of mammals will be suitable subjects, including rodents (e.g., mice, rats, hamsters), rabbits, primates, and swine such as inbred pigs and the like. The term "living subject" refers to host or organisms noted above that are alive. The term "living subject" refers to the entire host or organism and not just a part excised (e.g., a liver or other organ) from the living subject.

As used herein, the terms "optional" or "optionally" means that the subsequently described event or circumstance can or cannot occur, and that the description includes instances where said event or circumstance occurs and instances where it does not.

As used herein, "kit" means a collection of at least two components constituting the kit. Together, the components constitute a functional unit for a given purpose. Individual member components may be physically packaged together or separately. For example, a kit comprising an instruction for using the kit may or may not physically include the instruction with other individual member components. Instead, the instruction can be supplied as a separate member component, either in a paper form or an electronic form which may be supplied on computer readable memory device or downloaded from an internet website, or as recorded presentation.

As used herein, "instruction(s)" means documents describing relevant materials or methodologies pertaining to a kit. These materials may include any combination of the following: background information, list of components and their availability information (purchase information, etc.), brief or detailed protocols for using the kit, trouble-shooting, references, technical support, and any other related documents. Instructions can be supplied with the kit or as a separate member component, either as a paper form or an electronic form which may be supplied on computer readable memory device or downloaded from an internet website, or as recorded presentation. Instructions can comprise one or multiple documents and are meant to include future updates.

As used herein, "attached" can refer to covalent or non-covalent interaction between two or more molecules. Non-covalent interactions can include ionic bonds, electrostatic interactions, van der Walls forces, dipole-dipole interactions, dipole-induced-dipole interactions, London dispersion forces, hydrogen bonding, halogen bonding, electromagnetic interactions, $\pi$-$\pi$ interactions, cation-$\pi$ interactions, anion-$\pi$ interactions, polar $\pi$-interactions, and hydrophobic effects.

As used herein, "dose," "unit dose," or "dosage" can refer to physically discrete units suitable for use in a subject, each unit containing a predetermined quantity of a disclosed compound and/or a pharmaceutical composition thereof calculated to produce the desired response or responses in association with its administration.

Further definitions are provided in context below. Unless otherwise defined, all technical and scientific terms used herein have the same meaning as commonly understood by one of ordinary skill in the art of molecular biology. Although methods and materials similar or equivalent to those described herein can be used in the practice or testing of the present disclosure, suitable methods and materials are described herein.

Discussion

In accordance with the purpose(s) of the present disclosure, as embodied and broadly described herein, embodiments of the present disclosure, in some aspects, relate to NIR-II imaging probes for in vivo optical imaging. In embodiments, the NIR imaging probes are organic single molecular probes with the ability to track biologics, such as cells, including, for instance, single cells (e.g., stem cells, immune cells, donor cells, cancer cells, etc.) with a strong fluorescence signal with low cytotoxicity and long-term tracking ability with high temporospatial resolution. The present disclosure also includes pharmaceutical compositions including the NIR-II imaging probes of the present disclosure, cells including the NIR-II imaging probes, and compositions including NIR-II containing cells of the present disclosure. Systems and kits including the NIR-II imaging probes and compositions are also described herein. Methods of using the NIR-II imaging probes, compositions, systems, and kits of the present disclosure for imaging biological substances, cells, and the like, are also described in the present disclosure.

For instance, stem cells are pluripotent cells with self-renewing capacity, which can differentiate into a range of cell types under defined circumstances.(1-3) In practice, stem cell therapy is promising for treating numerous disorders (e.g., aging, autoimmune, and inherited disease) because autologous or allogeneic transplants can overcome the limitations of immune incompatibility.(4-9) To date, stem cell therapy has been intensively employed in the treatment of wounds, blood and cardiovascular diseases, cartilage defect, diabetes, et al. Recently, stem cell therapy was on track for approval for human use in Japan for damaged corneas.(10-17) However, one roadblock preventing further widespread applications of stem cell therapy is the difficulty in tracking cell fates upon transplantation, preventing early assessment of dosage, retention, and therapeutic efficacy. Addressing this issue would greatly benefit the prognosis and overall outcomes.(18) Hence, it is of great significance to track stem cells both in vitro and in vivo with high temporal and spatial resolution in a real-time manner during a prolonged period.

Noninvasive cell tracking is incredibly useful in stem cell therapy, including both direct and indirect labeling techniques.(19) By utilizing magnetic resonance imaging (MRI), single-photon emission computed tomography imaging (SPECT), positron emission tomography-computed tomography (PET-CT), and optical imaging, direct labeling strategies possess the advantages of abundant cell trackers and minimal interference with cells.(20, 21) In practice, each cell tracking approach has its unique strengths and weakness. For instance, superparamagnetic iron oxides (SPIOs) as MRI trackers can ensure excellent anatomic information in deep organs, but the signal becomes ambiguous when cell numbers are low.(22, 23) PET/CT detection is ultrasensitive, but they are potential ionizing hazards with relatively low temporal resolution.(24, 25)

On the other hand, fluorescence imaging enjoys the merits of high sensitivity, high temporal resolution, and excellent maneuverability, which promotes their broad applications in a variety of biomedical imaging tasks in animal models. To realize in vivo, noninvasive, deep tissue fluorescence imaging with high temporal-spatial resolution, exogenous probes with emission in near-infrared (NIR) region are preferred. (26) Specifically, great attention has been attracted to explore fluorescence probes in the second near-infrared (NIR-II) region (1000-1700 nm), which shows further improved tissue penetration depth and signal-to-noise ratio. (27) The first-in-human NIR-II fluorescence imaging-guided liver tumor surgery was recently described using organic single molecular indocyanine green (ICG), showing its advantages over traditional NIR-I imaging in clinical applications.(28) But to date, most reported NIR-II probes are based on inorganic or organic nanomaterials: carbon nanotubes, quantum dots, and organic nanoparticles. This raises concerns over toxicity and surface modification complexity in in vivo imaging applications.(29, 30) NIR-II quantum dots ($Ag_2S$, PbS) for stem cell labeling have shown fine tracking results, but their unknown long-term toxicity brings substantial concerns due to the uncertain excretion of those heavy metal based inorganic nanoparticles.(31, 32)

In comparison, organic, single molecular probes have well-defined components, high purity, clear excretion pathways and low cytotoxicity, which facilitate their applications in translational research. Certain organic, NIR-II emissive molecules with good biocompatibility have been reported for vascular structure imaging.(33, 34) Advancing the use of organic NIR-II emissive molecules as cell trackers into the field of stem cell therapy would significantly aid the development of new stem cell therapies. However, it is believed that no organic NIR-II fluorescent trackers have yet been reported for in vivo stem cell tracking in literature.

NIR-II Optical Imaging Probes

The present disclosure provides NIR-II optical imaging probes that can be used, among other uses, for in vivo imaging and/or tracking of cells and/or other biologic substances. In embodiments, the NIR-II imaging probes of the present disclosure include an organic, biocompatible NIR-II emissive molecule including a small molecule, biocompatible NIR-II dye coupled to a protein carrier complex. The protein carrier complex can include a carrier protein and a cell-penetrating peptide.

The small-molecule, biocompatible NIR-II dye molecule can include NIR-II dye molecules such as, but not limited to, CH-4T, CH1055, other carboxyl NIR-II dyes, NIR-II cyanine dye molecules, other small molecule NIR-II fluorescent molecules, and combinations thereof. In embodiments, the biocompatible NIR-II dye molecule is CH-4T.

In the NIR-II probes of the present disclosure, the protein carrier complex can include both a carrier protein moiety and a cell penetrating moiety. In embodiment, the carrier protein moiety is a protein/peptide with the ability to transport proteins. In embodiments, the carrier protein can include proteins such as, but not limited to, a serum albumin protein. In embodiments, the carrier protein is an albumin protein, such as, but not limited to, human serum albumin (HSA), bovine serum albumin (BSA), derivatives thereof and the like.

In embodiments, the cell-penetrating moiety (or membrane-penetrating moiety) can be a cell-penetrating peptide (CPP). A CPP is a peptide sequence that facilitates transport of the imaging probe across cell membranes. In embodiments, the CPP facilitates cell uptake by various cell types, but in some embodiments, the CPP may be specific to a certain cell type or otherwise modified to specifically target a certain cell type. In embodiments, CPPs can include a peptide or a small molecule synthetic analogue. In embodiments, the CPP can be, but is not limited to, a trans-activator of transcription (Tat) peptide of HIV, or a derivative or segment thereof retaining cell membrane penetrating functionality. For instance, in some embodiments, the CPP can be a Tat peptide having a peptide sequence having at least 75% sequence identity with the sequence: RKKRRQRRRC (SEQ ID NO: 1). In embodiments, the CPP is a Tat peptide having at least 80%, at least 90%, at least 95%, or more, sequence identity with SEQ ID NO: 1.

In embodiments the NIR-II dye molecules is coupled to the carrier protein, which is coupled to the CPP. In embodiments the carrier protein is HSA or BSA, and the CPP is a Tat peptide (such as, but not limited to, SEQ ID NO: 1), and the HSA or BSA is conjugated with the Tat peptide through a carbodiimide-mediated coupling reaction. The carrier protein and CPP can be conjugated to form a complex and then mixed with the NIR-II molecule to couple the NIR-II dye molecule to the carrier protein-CPP complex. In embodiments the carrier protein-CPP complex is an HSA/BSA-Tat complex. In embodiments, the ratio of NIR-II dye:carrier protein:CPP is from about 0.5-1.5:0.5-1.5:0.5-1.5. In embodiments, the ratio is about 1:1:1. In embodiments, the NIR-II probe includes the NIR-II dye CH-4T, the carrier protein HSS, and the CPP Tat in a ratio of CH-4T:HSS:Tat of about 1:1:1.

NIR-II Pharmaceutical Imaging Compositions, Kits, and Systems

The present disclosure also includes pharmaceutical compositions including a plurality of the NIR-II optical imaging probes of the present disclosure and a pharmaceutically acceptable carrier. Such pharmaceutical compositions can be used for imaging various cells and/or other biological substances. In embodiments, the probes can be configured to target specific types of cells, tissues, biomolecules, or other biological substances. In embodiments, the probes are configured to target specific cells, such as immune cells or cancer cells.

In embodiments for tracking specific cells in vivo or in vitro, the target cells can be combined with the NIR-II optical imaging probes prior to introduction into a subject and/or a substance to be imaged. In embodiments, cells to be tracked can include exogenous cells, such as stem cells, immune cells, donor cells to be introduced to a subject. Thus, embodiments of the present disclosure include a cell including one or more of the optical imaging probes of the present disclosure. In embodiments the target cells to be tracked include a plurality of the NIR-II imaging probes so that upon proliferation, subsequent generations of cells will also contain one or more of the NIR-II imaging probes to enable continued cell tracking following multiple generations of the exogenous cells after administration to a subject. In embodiments, cells of the present disclosure including the NIR-II optical imaging probes can include, but are not limited to, stem cells, pluripotent cells, immune cells, donor cells, cancer cells, and the like. Additionally, pharmaceutical compositions of the present disclosure can also include a plurality of target cells, where at least a portion of the target cells each include one or more of the NIR-II optical imaging probes of the present disclosure and a pharmaceutically acceptable carrier.

The present disclosure also provides for kits for imaging, where the kit can include a pharmaceutically acceptable imaging composition of the present disclosure (including either the NIR-II imaging probes and/or cells including the NIR-II imaging probes) and instructions for administration of the pharmaceutically acceptable imaging composition to a subject and imaging the subject. In embodiments, the subject can be a human or animal subject.

NIR-II imaging systems are also provided in the present disclosure, where the imaging systems can include the NIR-II probes of the present disclosure, cells including the NIR-II probes of the present disclosure, and/or a pharmaceutically acceptable imaging composition of the present disclosure and an imaging system configured to detect fluorescence in a second near infrared range of about 1000-1700 nm.

Imaging Methods

Methods of imaging cells and/or other biological substances in an animal (e.g., mammal, etc.) or human subject are also provided in the present disclosure. Although it will be understood that the NIR-II probes of the present disclosure can also be used ex vivo to image biological substances, the described NIR-II probes provide great advantages for in vivo, real-time imaging/tracking of substances in subjects that are not satisfied by other imaging probes. Thus, in embodiments, methods of the present disclosure include generating an image of a biological substance (e.g., cell, tissue, biomolecule, etc.) in an animal or human subject. In vivo imaging methods can include administering to an animal or human subject a pharmaceutically acceptable composition including a plurality of the NIR-II optical imaging probes of the present disclosure and obtaining an image of the location of the NIR-II optical imaging probes in the animal or human subject by detecting and imaging the fluorescent signal.

In embodiments of the imaging methods of the present disclosure, the NIR-II imaging probes are adapted to target a biological substance of interest in the subject. In other embodiments, the NIR-II imaging probe is already coupled to a biological substance of interest prior to introduction to the subject, such that the coupled biological substance (e.g., target cell, biomolecule, etc.) can be imaged and tracked in the subject. In embodiments, the target biologic substance can include, but is not necessarily limited to substances such as cells, tissues, small molecule therapeutics, and biomolecules. In embodiments, the biologic substance is a cell selected from the group consisting of: an immune cell, a stem cell, a pluripotent cell, a donor cell, and a cancer cell.

In some embodiments, such as mentioned above, the NIR-II imaging probes of the present disclosure are coupled to a biological substance of interest prior to introduction to the subject in order to track the substance in vivo after delivery/administration to the subject. In some such embodiments, the substance includes exogenous cells and the method includes in vivo imaging of the exogenous cells introduced to a human subject or animal. Such methods can include administering to the animal or human subject a pharmaceutically acceptable composition comprising a plurality of exogenous cells of interest (target cells), where the exogenous cells contain one or more of the optical imaging probes of the present disclosure. Thus, at least a portion of the exogenous cells administered to the subject include one or more optical imaging probes having a biocompatible NIR-II dye molecule coupled to an organic, biocompatible protein carrier complex including a carrier protein coupled to a cell-penetrating peptide (CPP). After administration of the pharmaceutically acceptable composition including the plurality of exogenous cells, the method further includes obtaining an image of the location of the NIR-II optical imaging probes in a tissue of the animal or human subject by detecting and imaging the detectable NIR-II fluorescence from the probes. Thus, the location of the NIR-II optical imaging probe indicates the location of the exogenous cells. In embodiments, the cells can be, but are not limited to, cells such as human stem cells, human induced pluripotent stem-cell derived endothelial cells, mouse mesenchymal stem cells, donor cells, and immune cells. In embodiments obtaining an image of the location of the NIR-II optical imaging probes includes imaging at least a portion of the patient with an imaging system configured to detect fluorescence in a second near infrared range of about 1000-1700 nm.

The imaging can be discrete (providing snapshot images of the location of the probes/cells) or it can also be continuous, allowing real-time tracking of the cells, or a combination of both. The imaging methods of the present disclosures allow in vivo imaging/tracking of the movement and/or proliferation of exogenous cells (or other exogenous substances) containing/coupled to the NIR-II optical imaging probes of the present disclosure. Thus, these probes and methods can provide the ability to safely and easily track exogenous cells, such as donor cells, stem cells, immune cells, and the like and determine their movement, location, and proliferation. As described in the example below, the fluorescent signal from the NIR-II probes can last for substantial periods of time, such as about 20 days or more, 30 days or more, etc. allowing long-term tracking of cells in a subject.

The example below provides additional detail and demonstration of the use of embodiments of the NIR-II imaging probes of the present disclosure for labeling, imaging, and tracking stem cells in vivo, allowing real-time tracking of the migration and distribution with single cell cluster resolution. Aspects of the present disclosure are described in greater detail below and in the accompanying examples and figures.

Although the methods described herein are described primarily with reference to in vivo imaging in a subject, it is possible that the imaging probes of the present disclosure could be adapted for generating pH responsive image (in vitro or in vivo in a tissue or other medium). Also, due to the accumulation of the imaging probes of the present disclosure in tumors and other cancerous tissue and the hollow configuration of the probes, the probes may also be adapted for use as a delivery vehicle for an active agent (e.g., chemotherapeutic agent, and the like).

Additional details regarding the methods, compositions, and organisms of the present disclosure are provided in the Examples below. The specific examples below are to be construed as merely illustrative, and not limitative of the remainder of the disclosure in any way whatsoever. Without further elaboration, it is believed that one skilled in the art can, based on the description herein, utilize the present disclosure to its fullest extent.

It should be emphasized that the embodiments of the present disclosure, particularly, any "preferred" embodiments, are merely possible examples of the implementations, merely set forth for a clear understanding of the principles of the disclosure. Many variations and modifications may be made to the above-described embodiment(s) of the disclosure without departing substantially from the spirit and principles of the disclosure. All such modifications and variations are intended to be included herein within the scope of this disclosure and protected by the following claims.

The following examples are put forth so as to provide those of ordinary skill in the art with a complete disclosure and description of how to perform the methods and use the compositions and compounds disclosed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding according to significant figures of the numerical value. In addition, the phrase "about 'x' to 'y'" includes "about 'x' to about y".

EXAMPLES

Now having described the embodiments of the disclosure, in general, the examples describe some additional embodiments. While embodiments of the present disclosure are described in connection with the example and the corresponding text and figures, there is no intent to limit embodiments of the disclosure to these descriptions. On the contrary, the intent is to cover all alternatives, modifications, and equivalents included within the spirit and scope of embodiments of the present disclosure.

Example 1—NIR-II Imaging Probe and Dynamic Imaging of Transplanted Stem Cells

Description

To address the challenges faced by conventional approaches for imaging stem cells in vivo in real time, the present example described, for the first time, a single molecular cell tracker with a strong fluorescence signal in the second near-infrared (NIR-II) window (1000-1700 nm) for real-time monitoring of in vivo cell behaviors in both healthy and diseased animal models.

The present example describes a novel NIR-II probe according to the present disclosure, referred to herein as "CelTrac1000," and demonstrates the use of CelTrac1000 for tracking stem cells in animal models. CelTrac1000 includes a human serum albumin (HSA) molecule incorporated with a small molecule NIR-II dye (CH-4T) and further derivatized with a Tat peptide (FIG. 1A). The structure of the single molecular tracker, CelTrac1000 can be precisely controlled and its synthesis can be easily scaled up. The toxicity, stability, and labeling efficiency of CelTrac1000 were first evaluated in cell models, showing that it could efficiently label stem cells within a few hours and stay in the cytoplasm for up to 30 days, with minimal leaking and perturbation to cell functions. Importantly, high resolution in vivo fluorescence imaging revealed the migration trajectory of administrated cells in the mouse circulation system with a single cell cluster resolution, which has never before been achieved. Furthermore, animal models of acute lung injury (ALI), myocardial infarction (MI) and middle cerebral artery occlusion (MCAO) were created. Direct imaging and comparisons of the transplanted stem cell distribution in the healthy and diseased models were successfully demonstrated and evaluated in high resolution and sensitivity.

The NIR-II tracker (CelTrac1000) has shown complete cell labeling with low cytotoxicity and profound long-term tracking ability for 30 days in high temporospatial resolution for semi-quantification of the biodistribution of primary mesenchymal stem cell and induced pluripotent stem cell-derived endothelial cells. The present example has also demonstrated CelTrac1000 as a simple and effective technique for ultrafast real-time tracking of the migration and distribution in a single cell cluster resolution, along with the lung contraction and heart beating. As such, it is believed that this this single molecular NIR-II tracker will shift the optical cell tracking approach into a single cell cluster and millisecond temporospatial resolution for better evaluation and understanding of stem cell therapy, affording optimal doses and efficacy. CelTrac1000 could greatly benefit pre-clinical and clinical translation, providing a novel biotechnique of ultrafast, long-term stem cell tracking as a breakthrough in this field.

Results

Synthesis and Characterization of CelTrac1000

The CelTrac1000 probe was synthesized through the incorporation of a NIR-II dye with a biocompatible protein carrier (FIG. 1A).

Figure 1B:
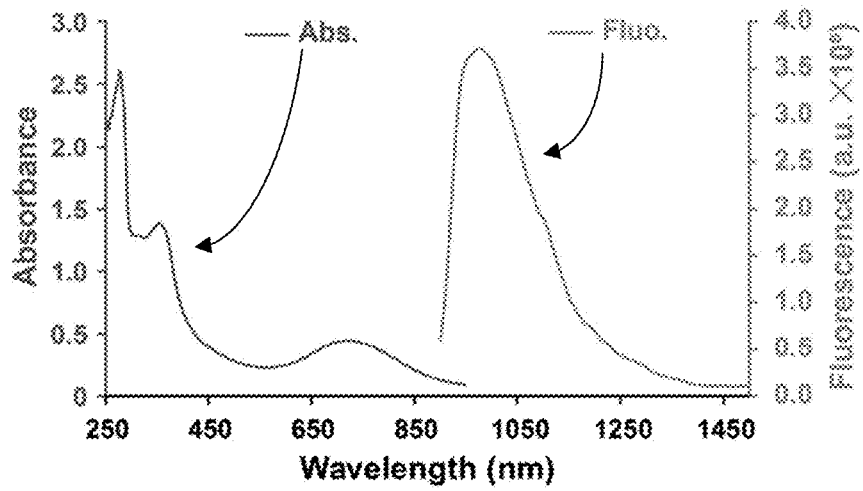
Figure 1C:
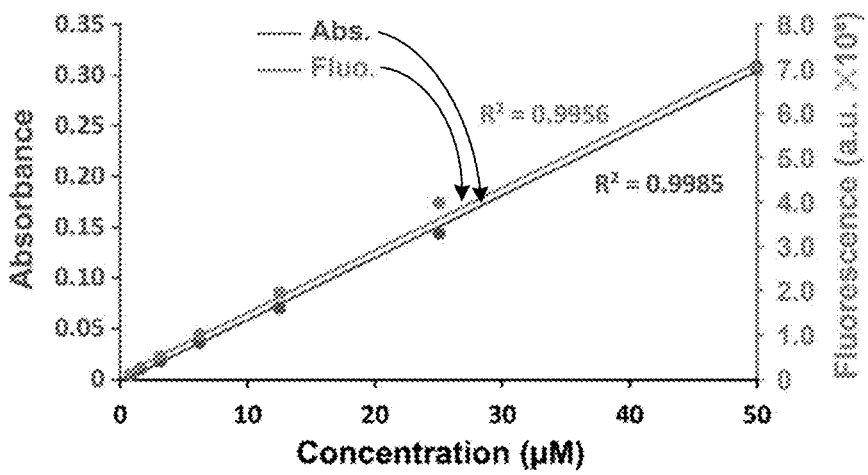

In brief, the NIR-II dye, CH-4T, was synthesized according to our previous report.(35, Antaris, et al., *Nat Commun* 8, 2017, incorporated herein by reference). Human serum albumin (HSA) was conjugated with Tat peptide (RKKRRQRRRC, SEQ ID NO: 1) through a carbodiimide-mediated coupling reaction to obtain Tat-HSA. The two components, CH-4T and Tat-HSA, were then mixed at equivalent concentrations and sonicated for 30 minutes (mins) in 1×PBS buffer at room temperature to produce CelTrac1000. The probe was analyzed by matrix-assisted laser desorption/ionization-time of flight mass spectrometry (MALDI-TOF-MS), suggesting it is a single molecular probe with a molar ratio of CH-4T:HSA:Tat at 1:1:1 (data shown in FIGS. S1-3 of provisional application 62/978,405, incorporated by reference herein). The optical properties of a CelTrac1000 were examined in aqueous solution, showing absorption and emission peaks at 750 and 1000 nm, respectively (FIG. 1B). Additionally, the absorbance and emission intensities of CelTrac1000 solutions showed a linear response to increased CelTrac1000 concentrations in a range of 0 to 50 µM (FIG. 1C). This linear relationship between fluorescence and concentration can be attributed to the protection of HSA, which can significantly reduce the severe aggregation-caused quenching effect of fluorescent molecules. This unique optical signature is key to fluorescence semi-quantitative analysis, which is very challenging in practice.

A successful cell tracker has both high labeling efficiency and low cytotoxicity at working concentrations to ensure reliable results for precise analysis. The direct labeling efficiency and toxicity of CelTrac1000 was evaluated on human induced pluripotent stem cell-derived endothelial cells (iPSC-ECs) and mouse mesenchymal stem cells (MSCs) to assess optimized feeding concentrations. When the feeding concentration of CelTrac1000 increased from 0.78 to 200 µM, enhanced uptake efficiencies were observed in both of iPSC-ECs and MSCs within 48 h (as shown in FIG. S4a of provisional application 62/978,405, incorporated above). On the other hand, the cell viability slightly decreased in both iPSC-ECs and MSCs when the concentration was above 100 µM (FIG. S4b of 62/978,405). To avoid this, 50 µM was settled on as the optimal feeding dose for the following stem cell labeling. In addition, the CelTrac1000 showed negligible shifts in the gene expression profiles of the endothelial markers of iPSC-ECs (CDH5, PECAM, NOS3, KDR, NRG1, and ICAM1) and biomarkers of MSCs (CD44, ENG, LY6A/SCA-1) after labeling for two weeks (data shown in FIG. S5 of the incorporated 62/978, 405 application).

In Vitro Cell Tracking

Figure 1D:
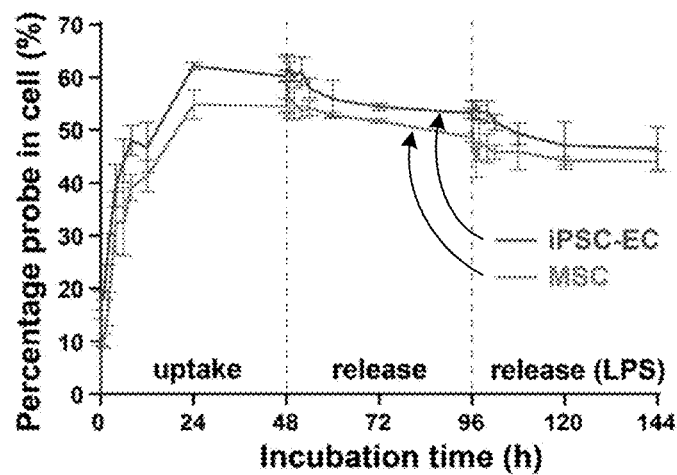

First, the fluorescence stability of CelTrac1000 was evaluated in the biological environment to mimic long-term in vivo cell tracking. After incubation in 1×PBS buffer at 37° C. for two months, CelTrac1000 still showed excellent fluorescence intensity with negligible changes in emission profiles (FIG. S6 of the incorporated 62/978,405 application). The uptake efficiency of CelTrac1000 in both iPSC-ECs and MSCs suggests that more than 40% of the probes (50 µM) were rapidly internalized into cells within the first 12 h (FIG. 1D). At 48 h post incubation, the internalization percentage of CelTrac1000 in ECs and MSCs was 60% and 55%, respectively. In addition, approximately 6-7% of the probe was released from the cells into the fresh culture medium in the following 48 h. Overall, CelTrac1000 has shown excellent cell uptake and retention ability.

Figure 1E:
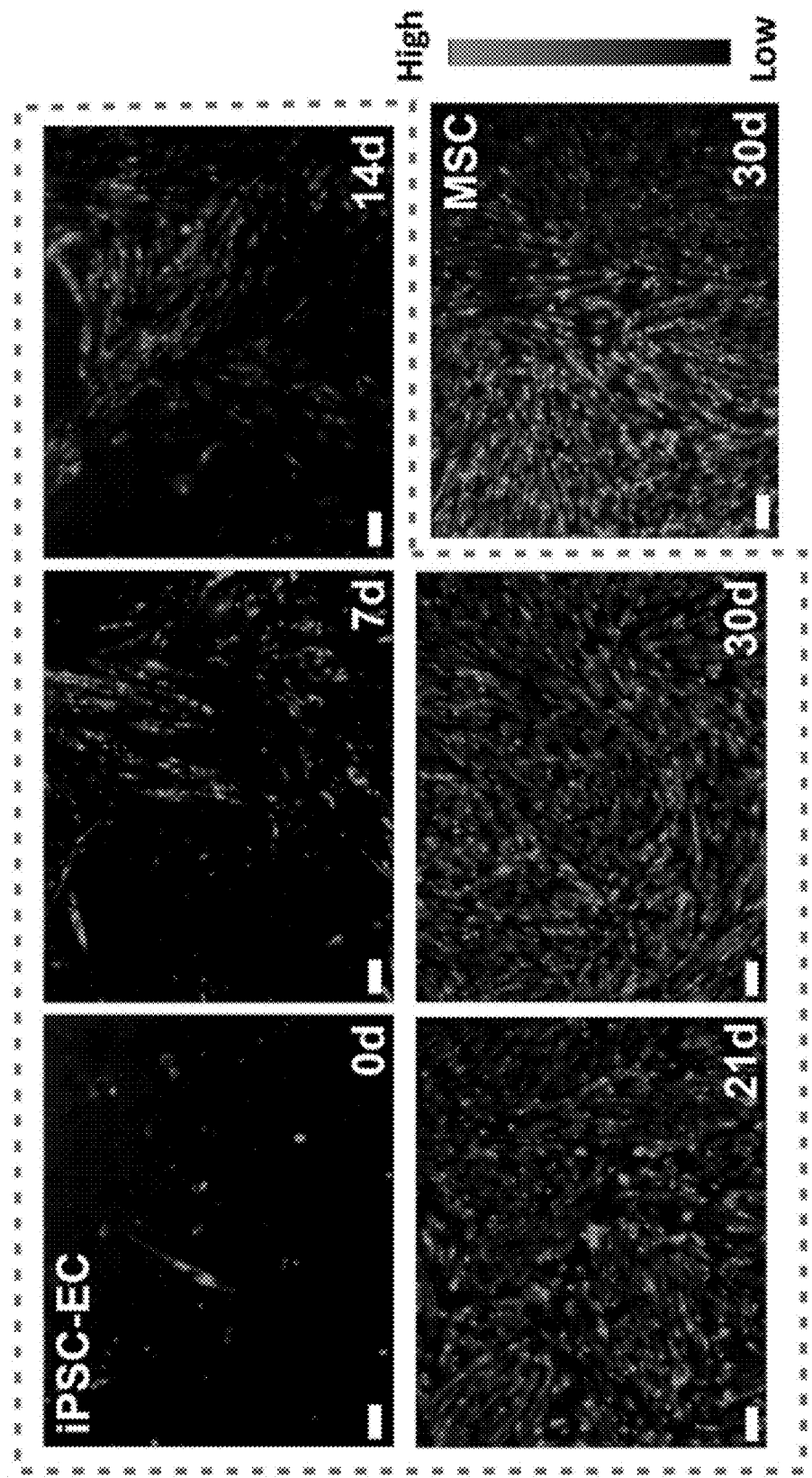

Customized NIR-II fluorescence microscopy was then used to study the performance of CelTrac1000 in vitro, tracking cells by recording fluorescence images of the labeled cells for up to 30 days post incubation. iPSC-ECs emitted intensive fluorescence with ~100% labeling efficiency after overnight incubation with CelTrac1000 (day 0 in FIG. 1E). Although the average fluorescence intensity from each EC gradually decreased due to cell proliferation in the next 30 days, almost all cells showed distinguishable fluorescence signals during the test period due to the excellent fluorescence stability and intracellular retention ability. The labeled MSCs also demonstrated a similar pattern of fluorescence changes in the in vitro culture, indicating a consistent performance of CelTrac1000 in the long-term labeling and tracking of different cell types. This is a significant advantage compared to commercial CellTracker and Qtracker, whose fluorescent signals only can last for a shorter period (~7 days) according to previously reported in vitro results.(36-38) As a result, the low toxicity, long-term tracking ability, and minimal leakage of CelTrac1000 presented it as a promising candidate for the next step of precise in vivo cell tracking.

In Vivo EC Tracking and Evaluation

Figure 1F:
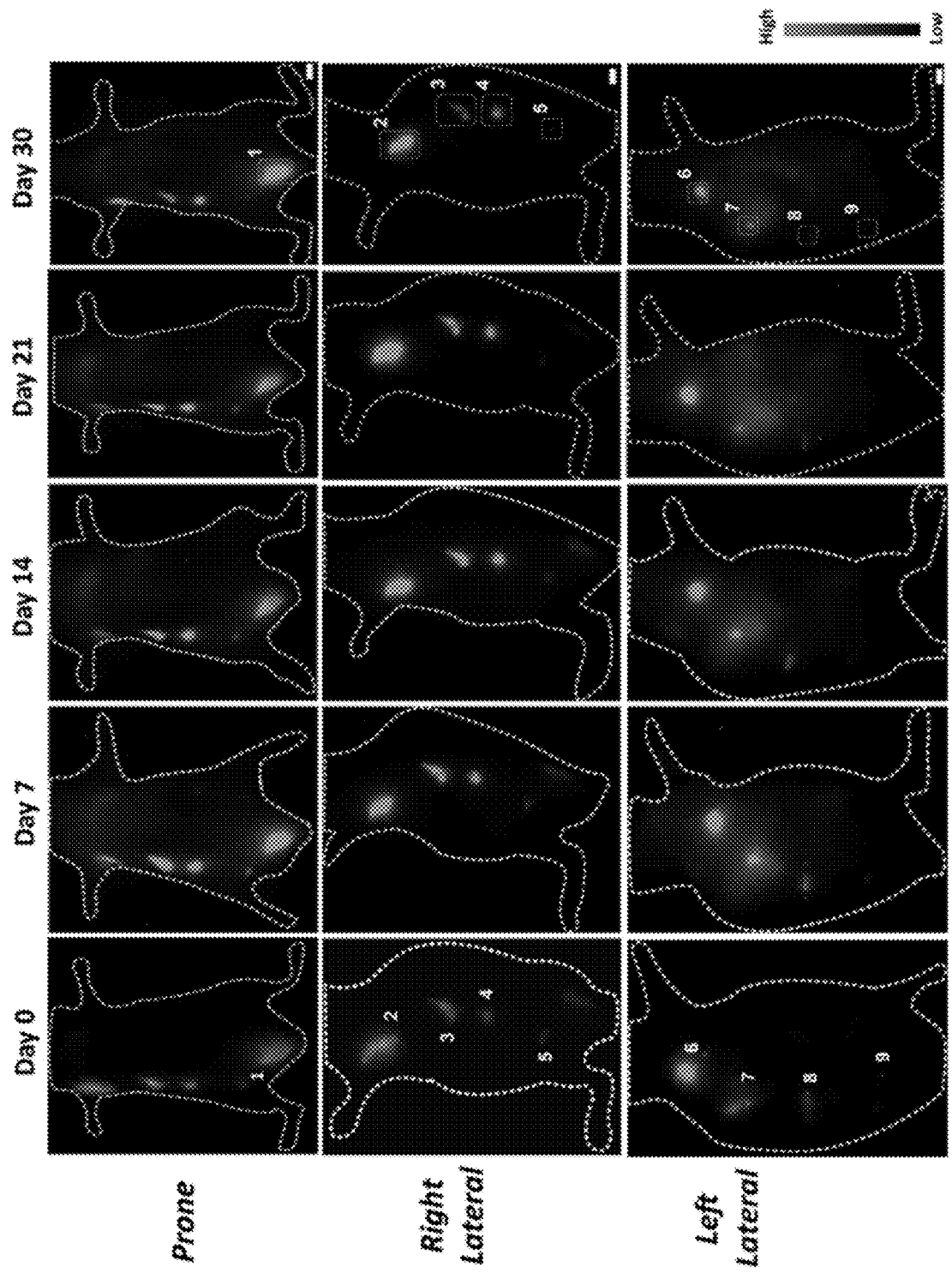
Figure 1I:
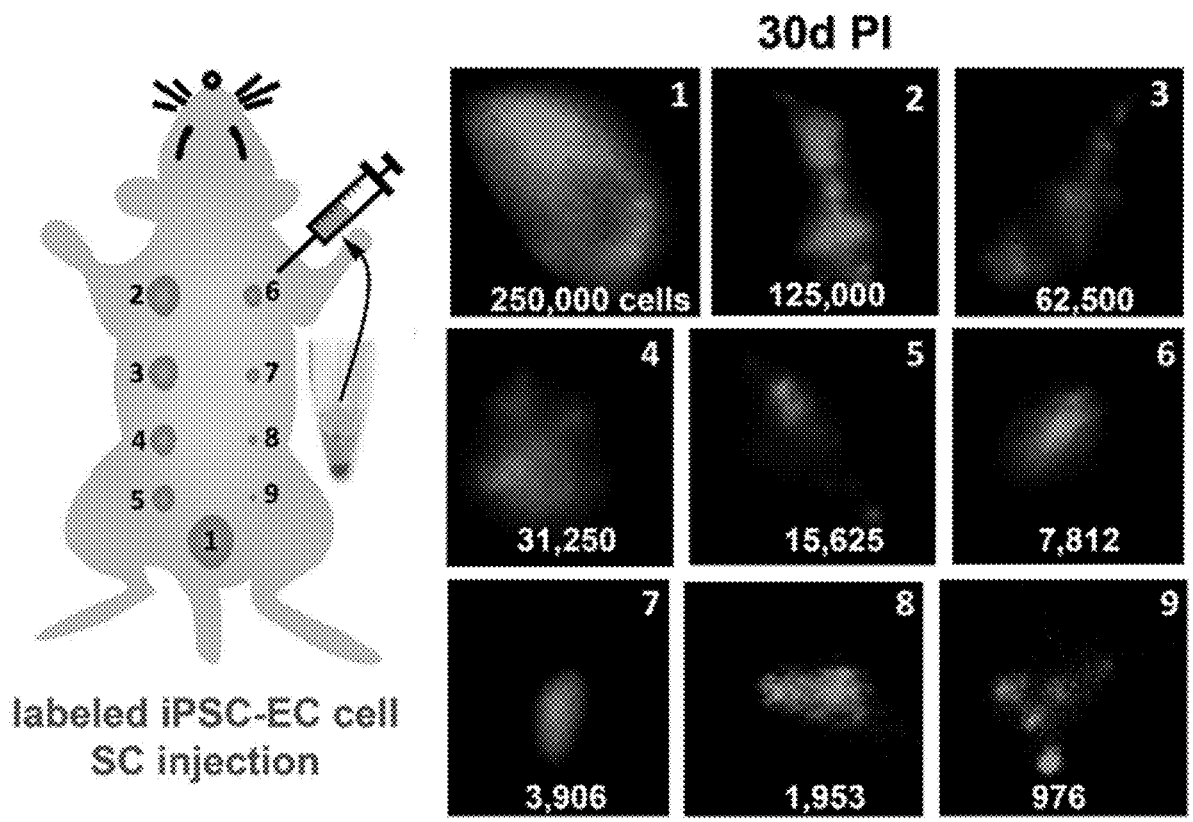
Figure 1I:
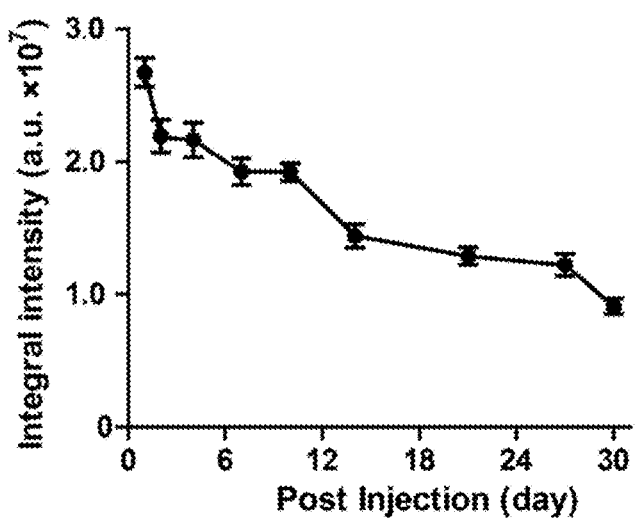
Figure 1J:
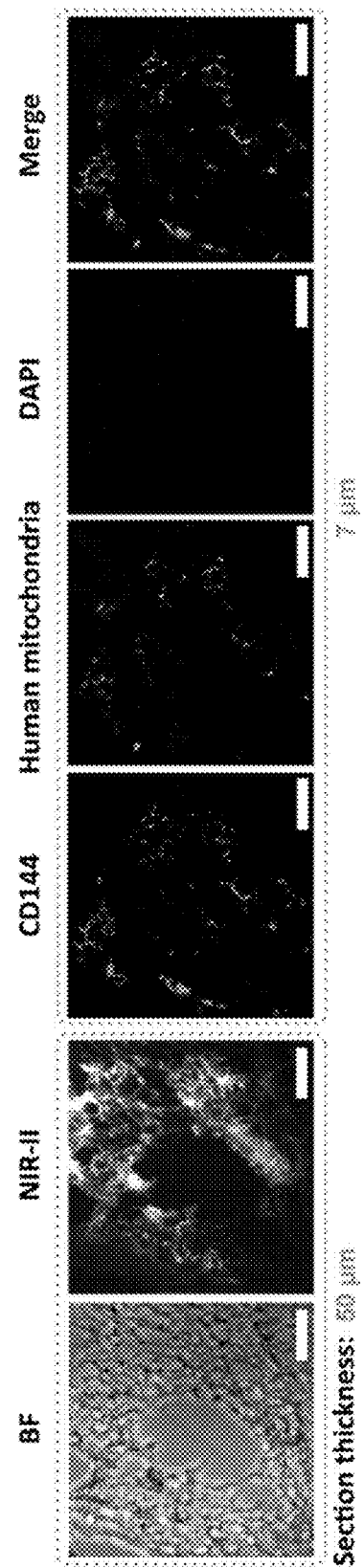
Figure 2A:
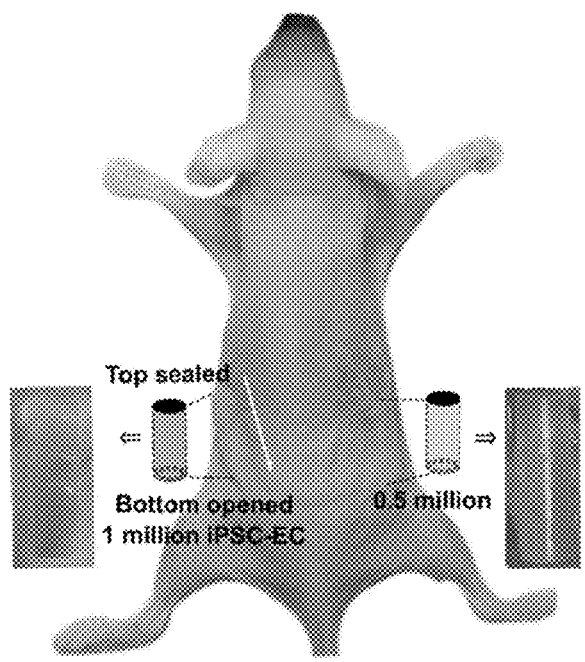
Figure 2B:
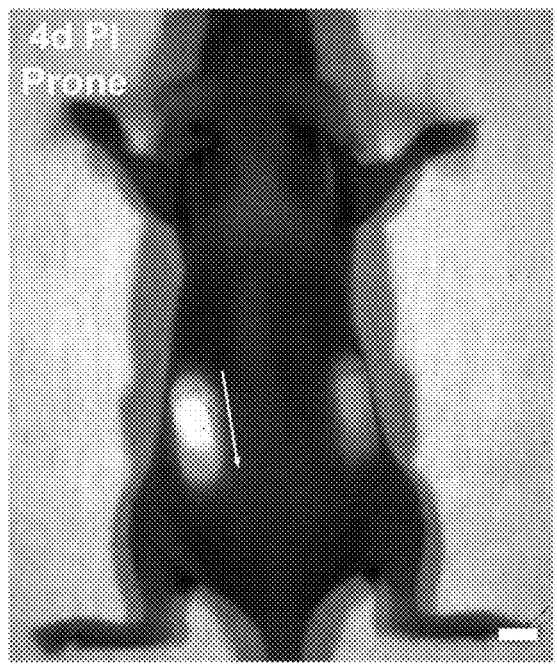
(FIGS. 2B, 2C) NIR-II fluorescent images (1000LP, 100 ms) of the same mouse 4 days and 30 days post angioreactor transplantation, respectively. The magnified NIR-II images show clear visualization of labeled iPSC-ECs in the reactor.
Figure 2C:
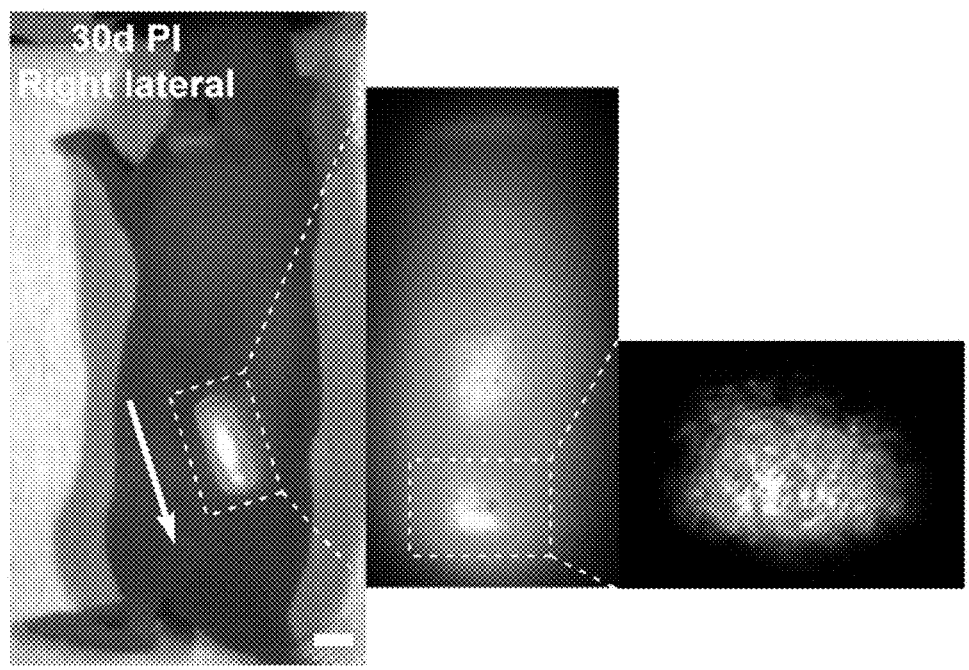
Figures 2J, 2K, 2L, 2M, 2N:
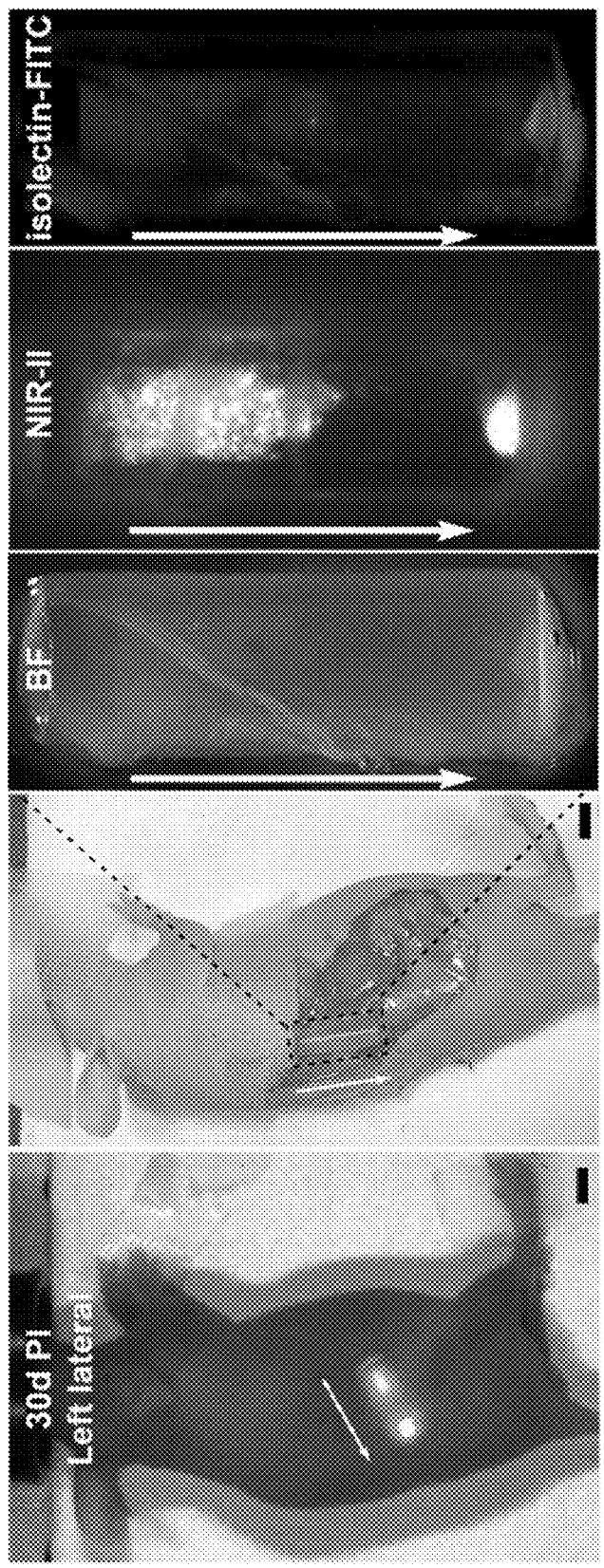
(FIGS. 2J-2N) NIR-II fluorescent images (1000LP, 100 ms) and immunofluorescent images of iPSC-EC after isolectin-FITC staining of the extracted angioreactor from the right lower back 30 days, post transplantation.

A series of in vivo studies were designed to assess the performance of CelTrac1000 in the long-term tracking of animal models. First, different numbers of CelTrac1000-labeled iPSC-ECs (250000, 125000, 62500, 31250, 15625, 7812, 3906, 1953, 976) were subcutaneously injected at 9 spots on the backs of nude mice (FIGS. 1F, G). Intense fluorescent signals from the injection spots can be clearly distinguished from day 0 to day 30 post-transplantation (FIG. 1F). Of note is all the injection sites emitted strong fluorescence on day 30 under a high magnification lens (FIG. 1H), confirming the ultra-sensitive and stable imaging abilities of NIR-II CelTrac1000 in animal models. The fluorescence intensity changes in this study were further semi-quantitatively analyzed through the integration of the fluorescence intensities. As shown in FIG. 1I, the integrated fluorescence intensity of spot one injected with 250,000 labeled ECs gradually decreased from day 0 to day 30, which was consistent with the previous studies. Analysis of spots 5 (15625 cells) and 9 (976 cells) as representative examples also demonstrated similar results (FIG. S7 of the incorporated 62/978,405 application). The skin tissues at injection sites were collected at day 30 and the transplanted cell clusters were observed under customized NIR-II fluorescence microscope (FIG. 1J). In addition, immunofluorescence staining of the tissue section suggests that a number of cells were double-positive with the expression of human mitochondria and endothelial cell marker CD144 (FIG. 1J), indicating that a certain number of human iPSC-ECs survived and engrafted during the test period. As such, labeling by CelTracker1000 did not affect the in vivo cell engraftment.

In the next step, a directed in vivo angiogenesis assay (DIVAA) was conducted to further visualize the in vivo angiogenesis of the iPSC-ECs. In brief, the semi-closed silicone angioreactors with a diameter of 5 mm were filled with a mixture of iPSC-EC and Matrigel, followed by subcutaneous implantation on both sides of the lower back of nude mice (FIGS. 2A-2F). The survival of the iPSC-ECs and their participation in new vessel formation was longitudinally tracked at a depth of ~4 mm for 30 days. Upon immunostaining of the iPSC-ECs in the transplanted angioreactors using isolectin-FITC, new vessel formation was observed from the iPSC-ECs 30 days post-surgery (FIG. 2H-2O). As such, these results validate the capability of transplanted iPSC-ECs to undergo angiogenesis as reported previously (39) as well as provide the precise time window for angiogenesis, which can be a useful tool for better evaluating regenerative therapy with iPSC-ECs.

Highly Sensitive and Efficient In Vivo MSC Tracking in the Circulation System

Figure 3C:
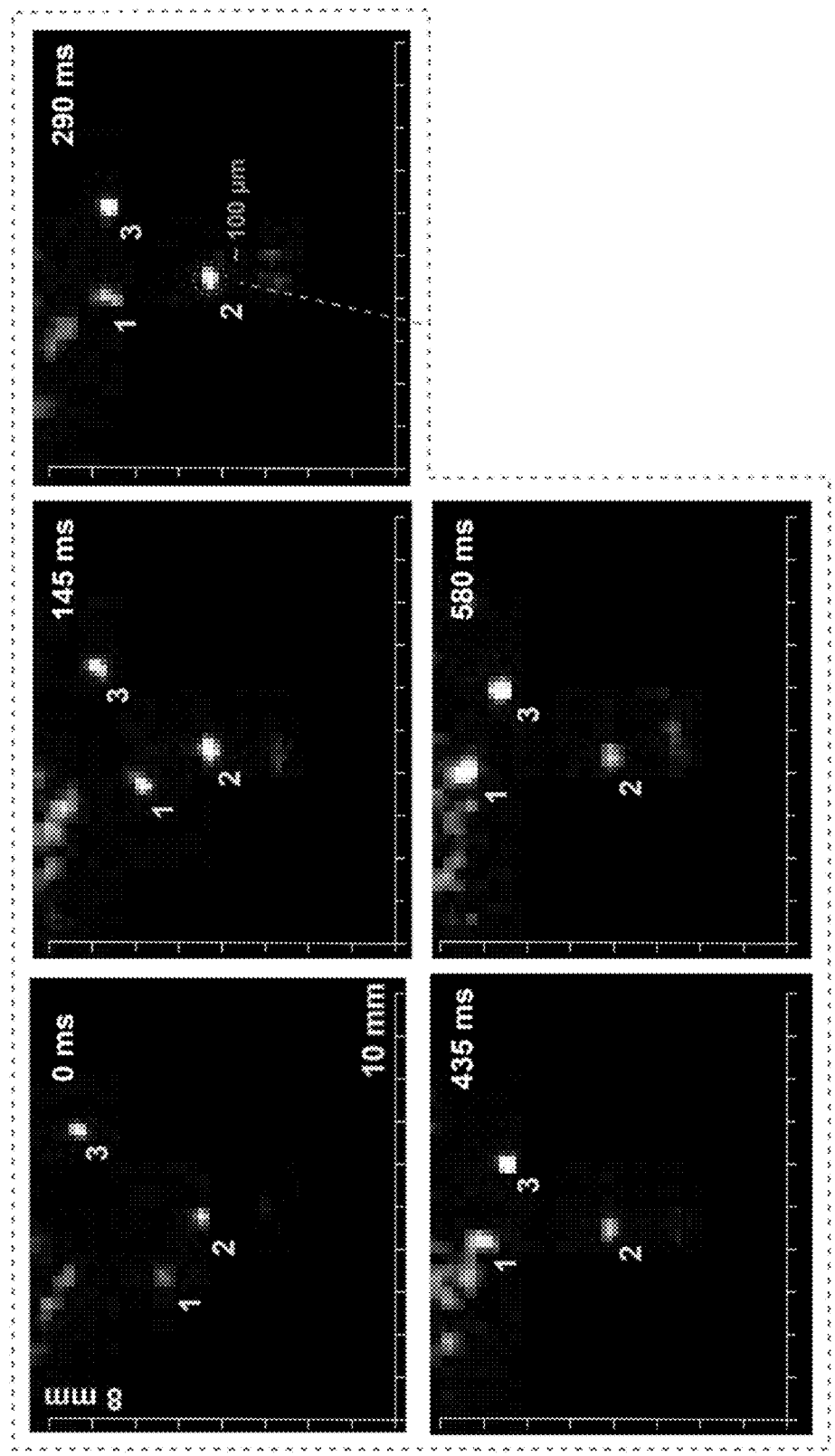

The whole body NIR-II fluorescence imaging was performed to track intravenously injected CelTrac1000-labeled MSCs to reveal the real-time cell migration in the circulatory system. 1,000,000 labeled MSCs were injected into the tail vein of each healthy mouse. The ultra-fast and sensitive NIR-II imaging systems allowed monitoring of the dynamic biodistribution of the administrated MSCs in real-time (FIGS. 3A-3K). The lung showed strong fluorescence signals immediately after MSC injection as the majority of administrated cells were initially trapped inside lung capillaries.(40) Later, the circulating MSCs gradually accumulated in the liver and spleen. More importantly, the real-time traffic of single-cell clusters at several positions in the circulation system was observed, as well as their migration through blood vessels from one organ to another. In particular, the migration of cells among the lungs, liver, and spleen, as well as the cell traffic within the hindlimb blood vessels could be clearly visualized. FIGS. 3A and 3B show the representative frames of fluorescence images from videos (not shown). The single-cell clusters in high resolution are visualized (FIG. 3A). Sequential frames in FIG. 3C clearly indicate the trajectory of three individual MSC clusters under magnification in the region highlighted in FIG. 3B, suggesting the ultra-high sensitivity of our in vivo cell tracking technique. To facilitate the estimation of cell numbers, it was assumed that a single MSC is in a cubic shape with a side length of ~10 μm. As the clusters shown in FIG. 3C suggest a dimension of ~100 μm, from the dimensions of the cell cluster, it is estimated that one single cell cluster captured on the NIR-II images contained ~1000 MSCs. However, considering the diffraction effect of light, one cell cluster observed under the imaging system could likely contain fewer cells. As a result, this approach can unveil in vivo cell migration behaviors in detail that would be impossible to be captured with conventional cell tracking techniques.

Figure 3D:
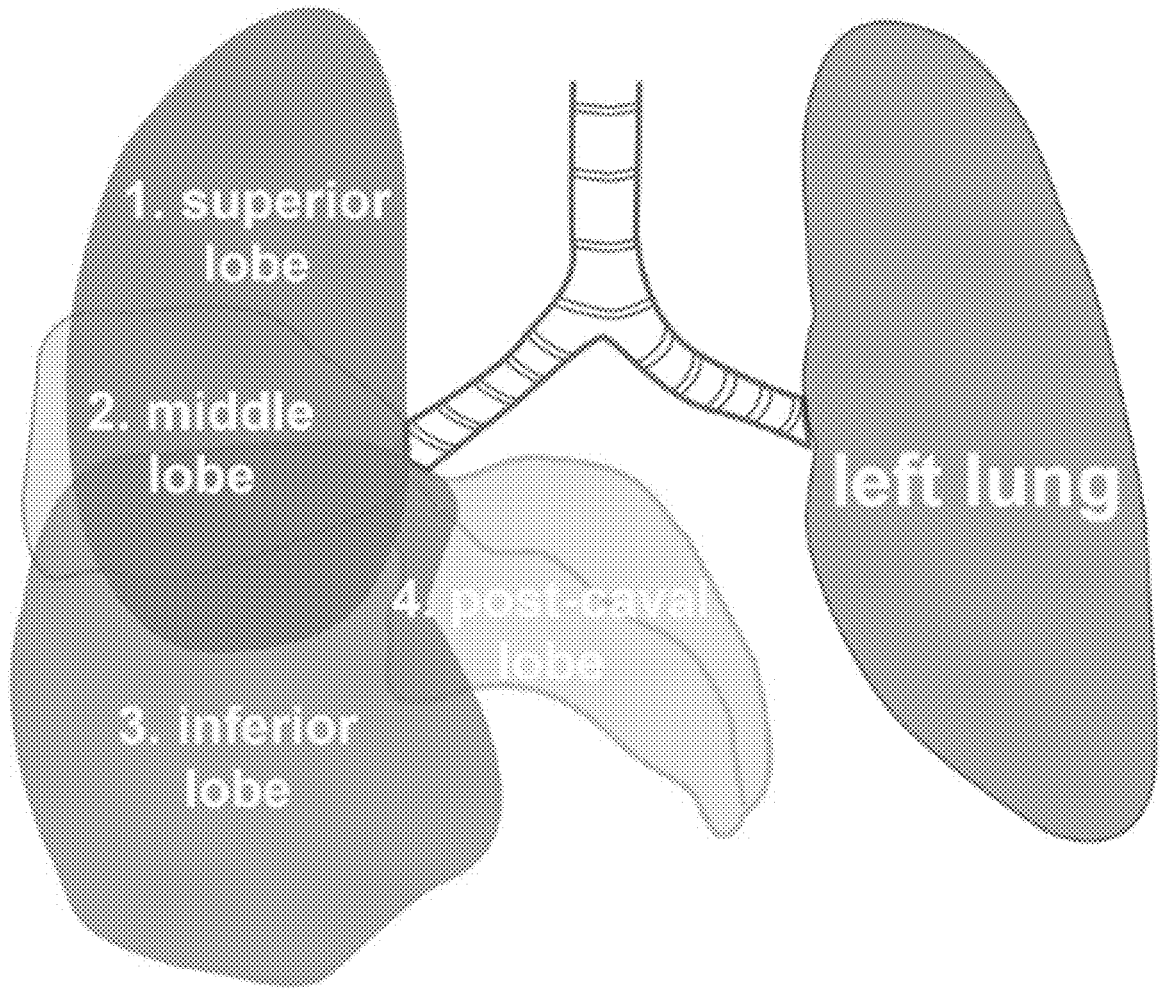
Figure 3H:
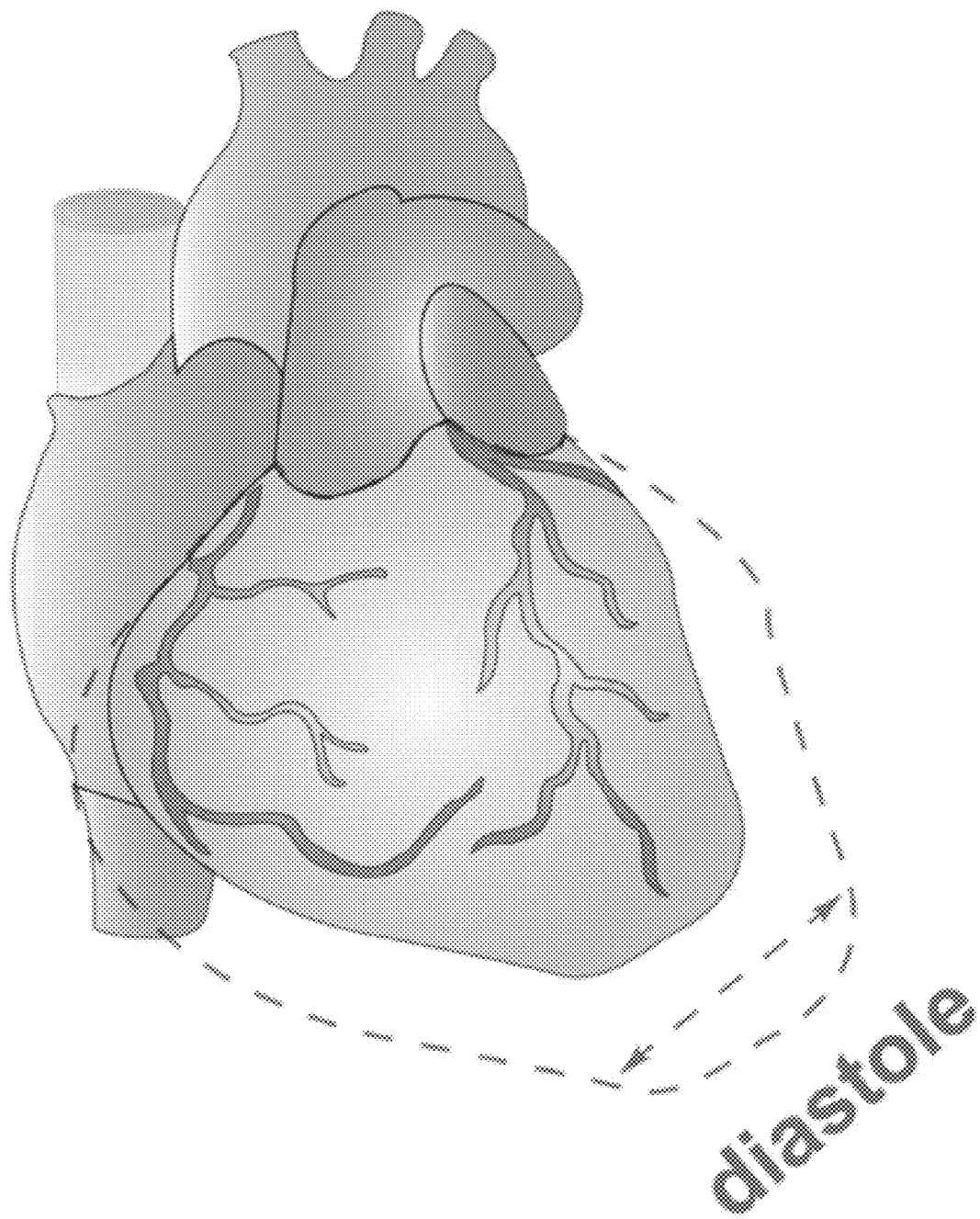
Figure 3L:
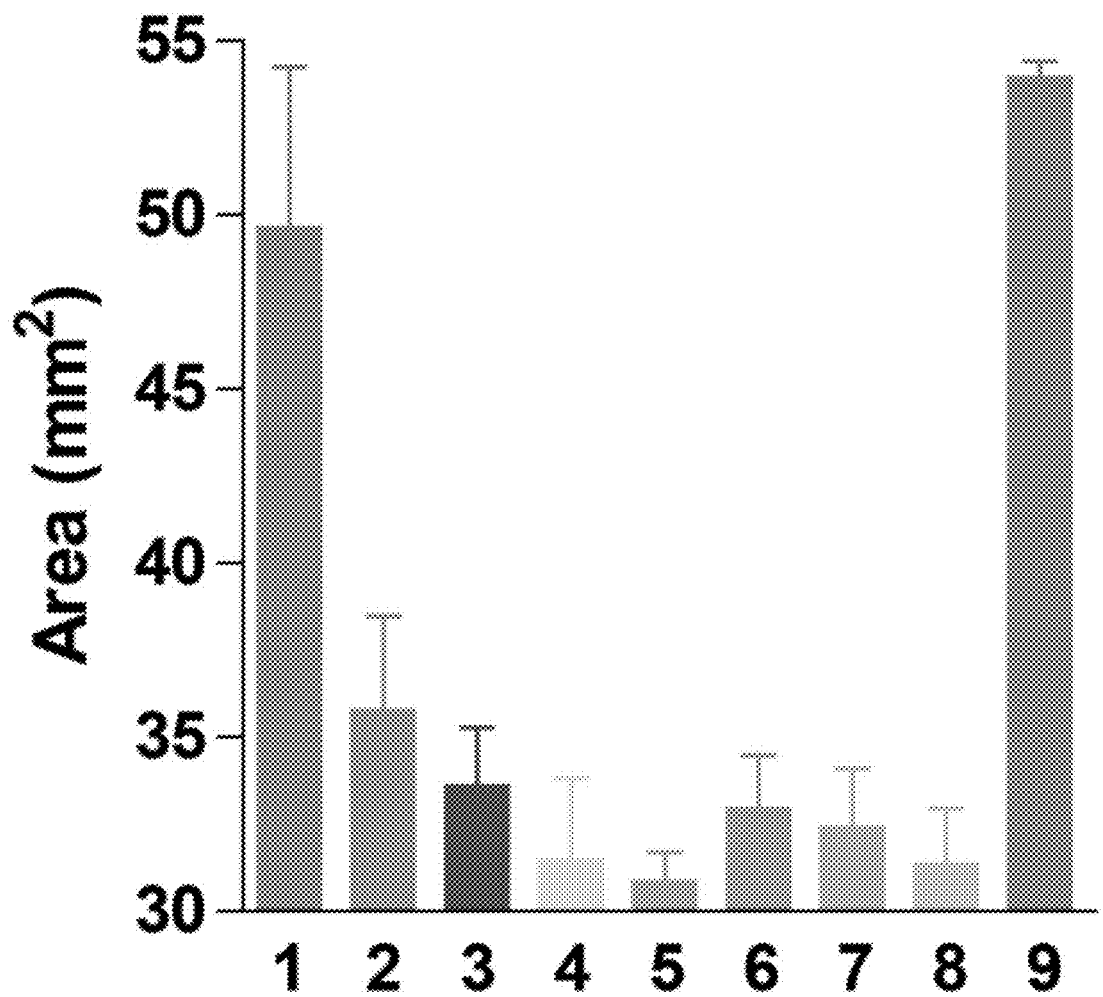

Furthermore, the movement of the right lung lobes during inhalation and exhalation was recorded in real-time when the mouse was placed in a lateral position (FIGS. 3D-F, video not shown). The schematic in FIG. 3D shows the structure of the right lung, consists of four lobes: the superior, middle, inferior, and post-caval lobes. The positions of four lobes relocate accordingly when breathing. Because of the high fluorescence intensity from the MSCs trapped in the lung, the movement of these lung lobes was captured under the ultra-fast NIR-II imaging system (FIG. 3F). The high-resolution images allowed extraction of the profile of each lobe and calculate the size change during the inspiration/expiration cycle (FIG. 3G). In addition, the mouse was placed in a supine position to enable recording of the heart beating throughout the full cardiac cycles. Due to the presence of administrated MSCs in blood and their strong NIR-II fluorescent signal, it was clearly observed and recorded the diastole and systole phases of the heart under anesthesia status (FIGS. 3H-L, video not shown). These results prove the highly efficient and accurate imaging of MSCs in the mouse circulation system, suggesting that the described NIR-II cell tracking system and approach can serve as a simple and promising technique to reveal obfuscated biological mechanisms and processes.

In Vivo MSC Tracking in Disease Models

Figure 4B:
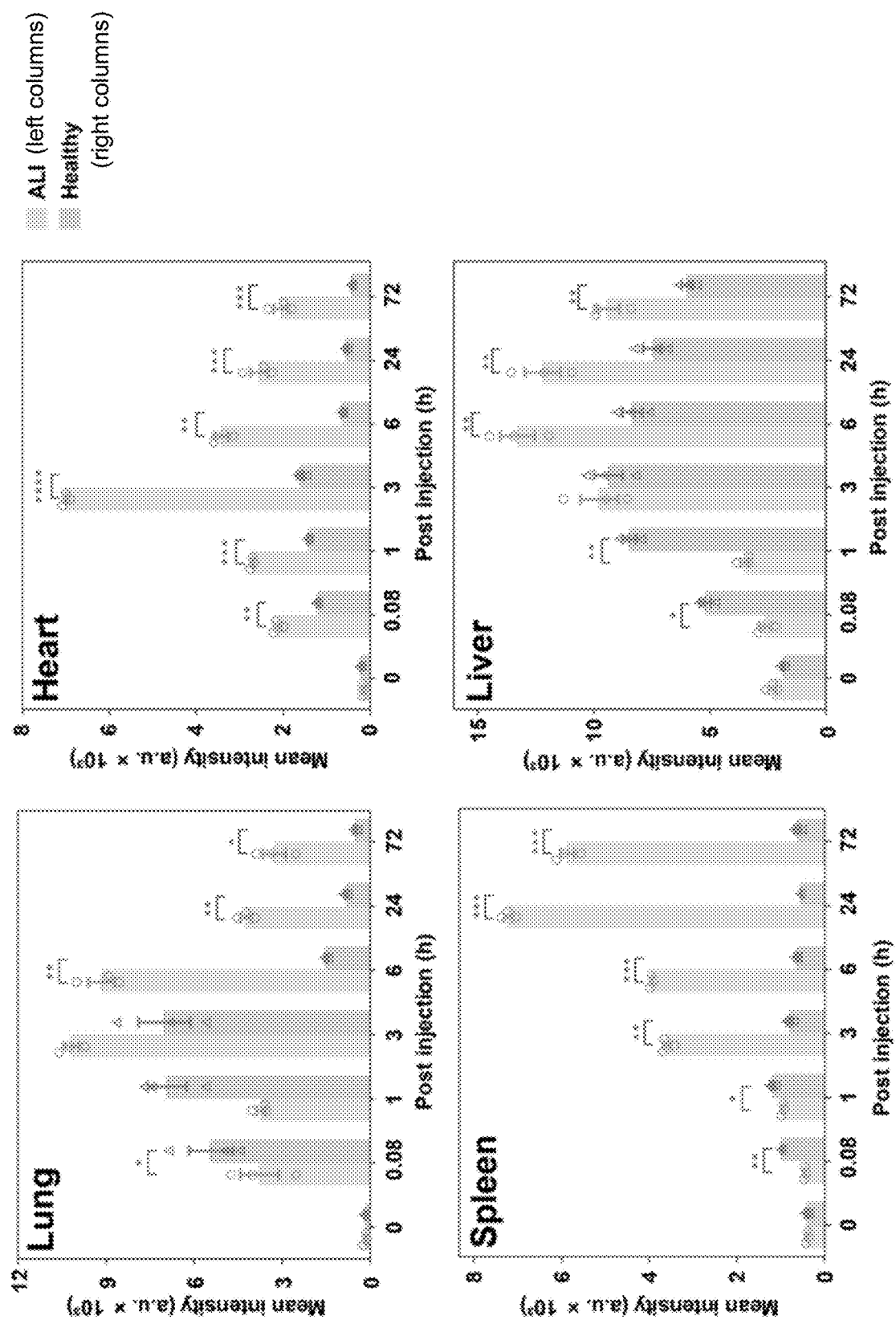
Figure 4C:
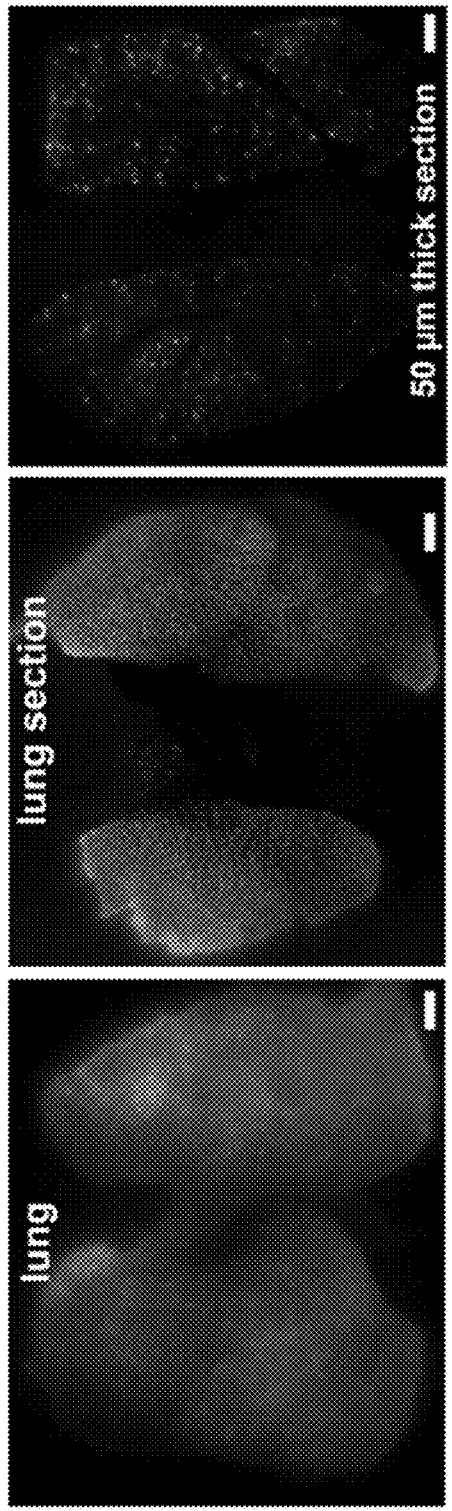
Figure 4D:
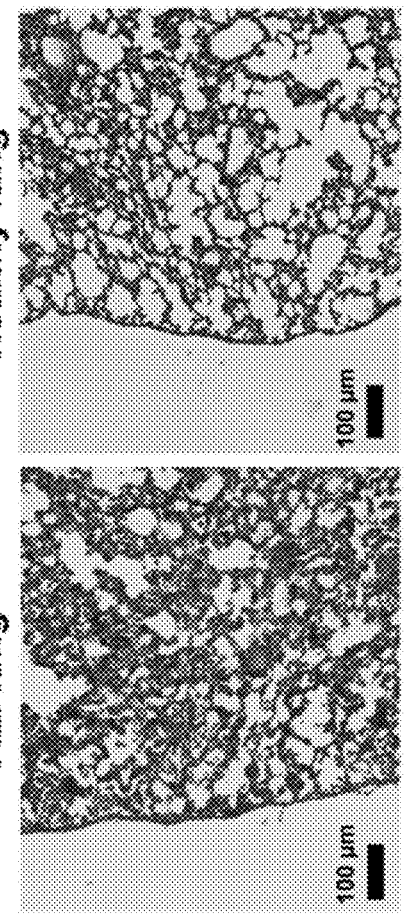
Figure 4F:
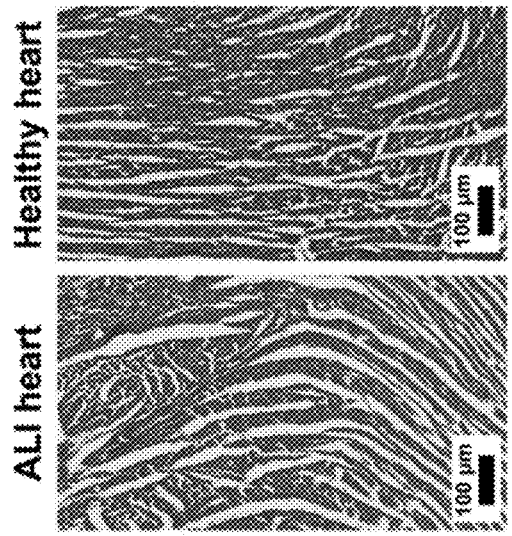
Figure 4H:
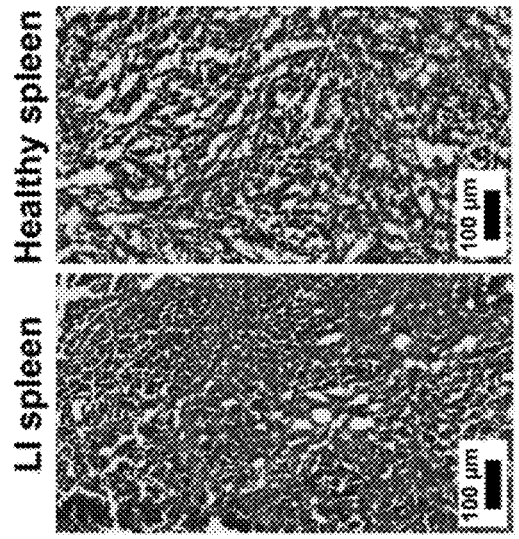
Figure 4E:
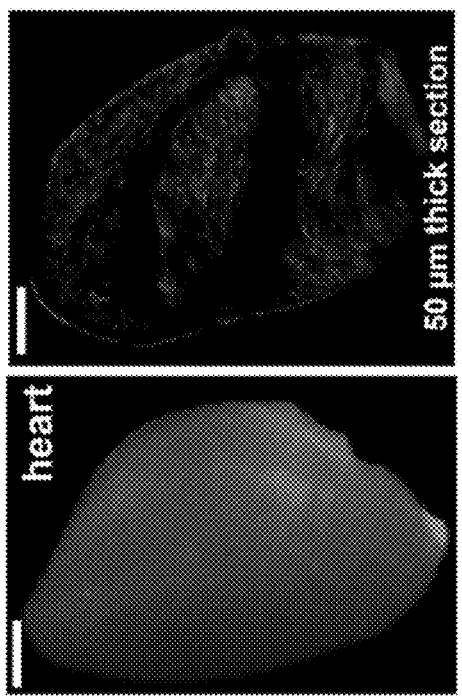
Figure 4G:
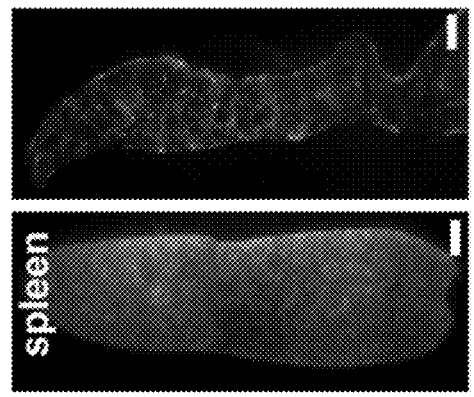

One intrinsic quality of MSC is their homing ability to injured sites, secreting a broad spectrum of paracrine factors to create a regenerative microenvironment.(41) The CelTrac1000 was thus used to evaluate the biodistribution and retention of labeled MSCs in injured mice of various disease models, including acute lung injury (ALI), myocardial infarction (MI), and middle cerebral artery occlusion (MCAO) model of stroke. All these models were confirmed through hematoxylin and eosin (H&E) staining examination. First, lipopolysaccharide (LPS) was used to create ALI in C57BL/6J mice through intratracheal instillation. Upon intravenous administration of the labeled MSCs (1 million) into ALI and healthy mice, NIR-II imaging studies were performed to monitor the dynamic changes of fluorescent signals in the animal bodies (FIG. 4A). Quantitative analyses was then carried out of the average fluorescent intensities in different organs using ImageJ, revealing the details of their dynamic cell migration and retention of the MSCs in the lung, heart, spleen, and liver (FIG. 4B). Ex vivo images of organs and H&E staining of sectioned tissues were acquired after in vivo imaging study on day 3 (FIGS. 4C-H). As shown in FIG. 4B, the lungs trapped a number of MSCs in both ALI and healthy mice in the first 5 mins post-injection. The fluorescence intensity from the injured lungs of ALI mice was significantly stronger compared to that from the healthy mice at 6 h post-injection. This can be mainly attributed to the homing capacity of MSCs to injured sites in the lung lobes, resulting in higher engraftment (FIGS. 4C-D). The MSC clusters could be clearly observed under the NIR-II imaging system in the lung tissue sections collected from the ALI mouse 72 h post cell administration (FIG. 4C). On the contrary, more MSCs escaped from lungs in the healthy control and re-entered into the circulation system, resulting in a rapid decrease in fluorescence intensity of the healthy lungs from 3 h post cell administration (FIG. 4B).

Surprisingly, the heart and spleen of ALI mice showed intense fluorescent signals after 3 h post-injection, with significant differences comparing to that of healthy mice. Looking at the heart, the fluorescent intensity of the heart from the ALI mice gradually increased until 3 h, then decreased thereafter. Of note is that the signals from the ALI heart were significantly stronger than those from the healthy heart at all time points post cell injection. These results could be due to the fact that cardiac dysfunction and damage was also caused in the LPS-induced ALI model, which prompted MSC migration and homing to the injured heart tissues(42). Similar results were observed in the spleen tissues, with significantly higher fluorescent intensity from injured spleen in ALI mice. At 72 h post cell injection, significant cell accumulation was observed in the liver and spleen, which are the primary excretory organs. As a result, these findings provided direct evidence to confirm that ALI model creation using LPS caused inflammation in major organs that led to the recruitment of MSCs.

Figure 5A:
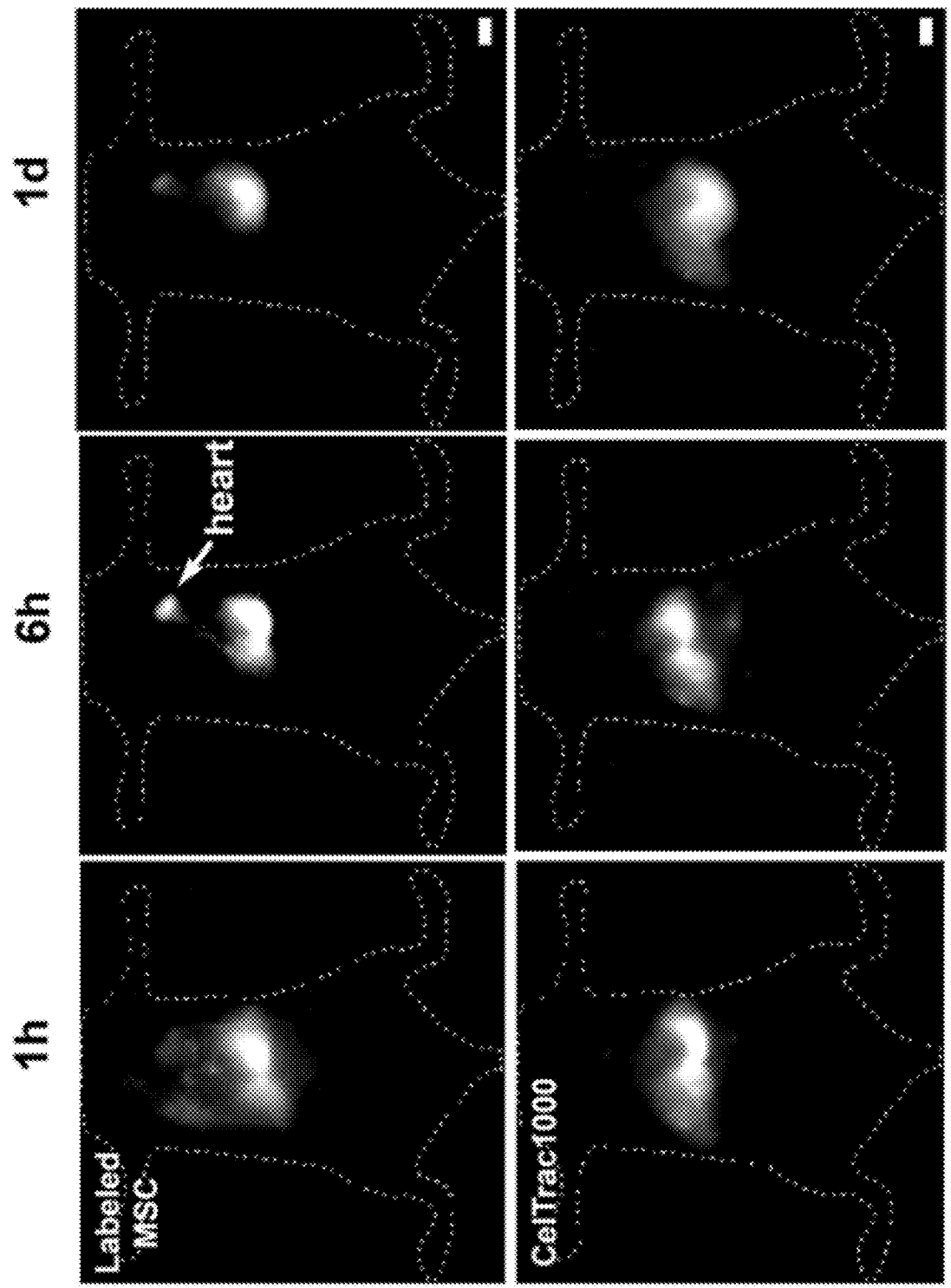
FIGS. 5A-5F illustrates imaging and analysis of the biodistribution of MSCs in the mouse model of myocardial infarction (MI).
Figure 5D:
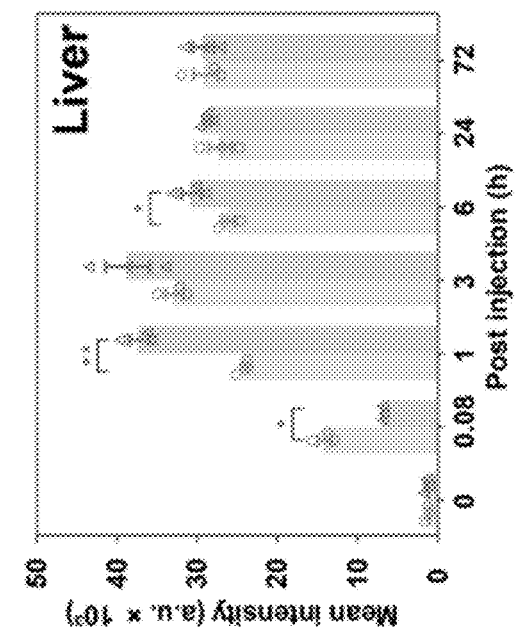
Figure 5B:
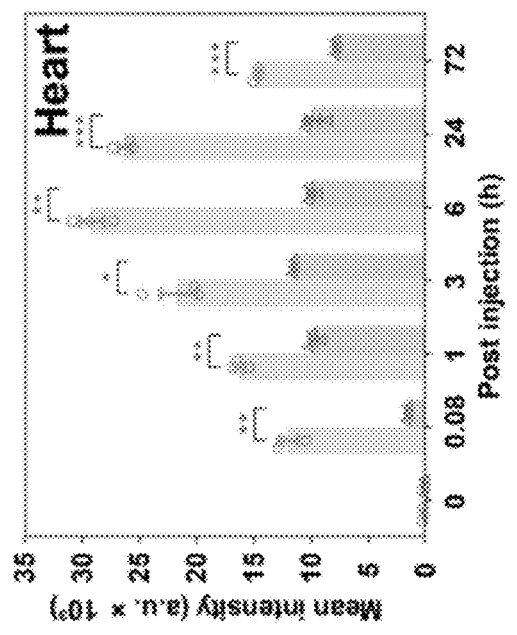
Figure 5C:
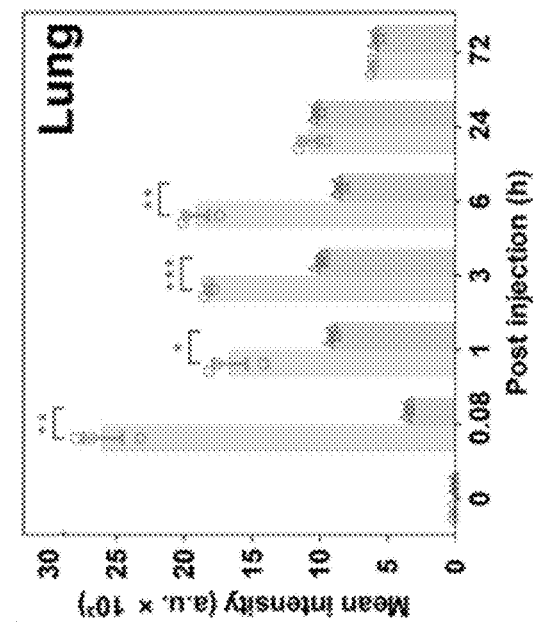
Figures 5E, 5F:
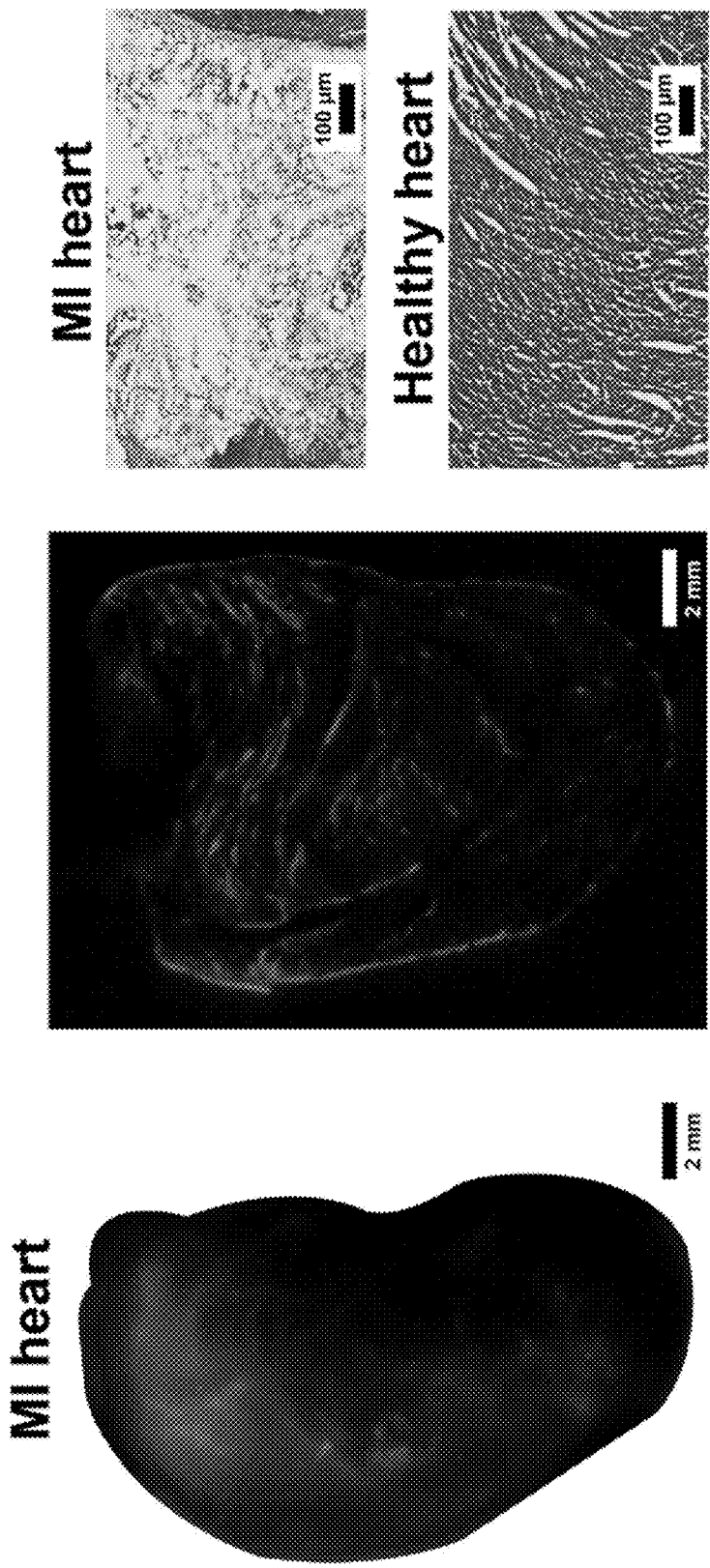

To further confirm if the homing of MSCs in heart tissues of ALI mice was caused by inflammation and injury, a MI mouse model was created for MSC transplantation. In a parallel experiment, CelTrac1000 was injected into the MI mice instead of labeled MSCs, for comparison. The biodistribution and dynamic behavior of the probe and MSCs in MI mice showed very distinct patterns (FIG. 5A). Similar to what was discovered in the ALI model, the administrated labeled MSCs in MI mice were trapped in the lung and heart immediately upon intravenous injection while the injected probe only showed minimal intensity in the lung and heart 5 mins post-injection (FIGS. 5B and 5C). The fluorescence signals from the hearts of MI mice gradually increased post CelTrac1000 injection. This could be caused by the high concentration of the probe in the blood, which when combined the higher blood vessel permeability of the injured heart tissues, may facilitate leakage of the probe, accumulating in the surrounding tissues. In addition, the relative fluorescence intensity ratio of heart to lung in the MI model was significantly higher than that of the ALI model 6 h post-MSC injection ($p<0.05$) (FIG. 4B, FIG. 5B, and FIG. 5C), due to the severer heart injury created in the MI model. The fluorescence signal from the heart was still high at 72 h post-MSC injection, suggesting the MSCs were preferentially attracted to the infarcted myocardium. This result was further confirmed from ex vivo fluorescence imaging and H&E staining results of heart tissue sections (FIGS. 5E and 5F). Meanwhile, the liver's signals remained at a high level from the initial injection up to 3 days in both CelTrac1000-injected and MSC-injected mice. Overall, the CelTrac1000 labeling strategy allowed monitoring of the dynamic migration and distribution of MSCs in a MI model, with high sensitivity and specificity, which has never before been achieved by fluorescence imaging.

Figure 6A:
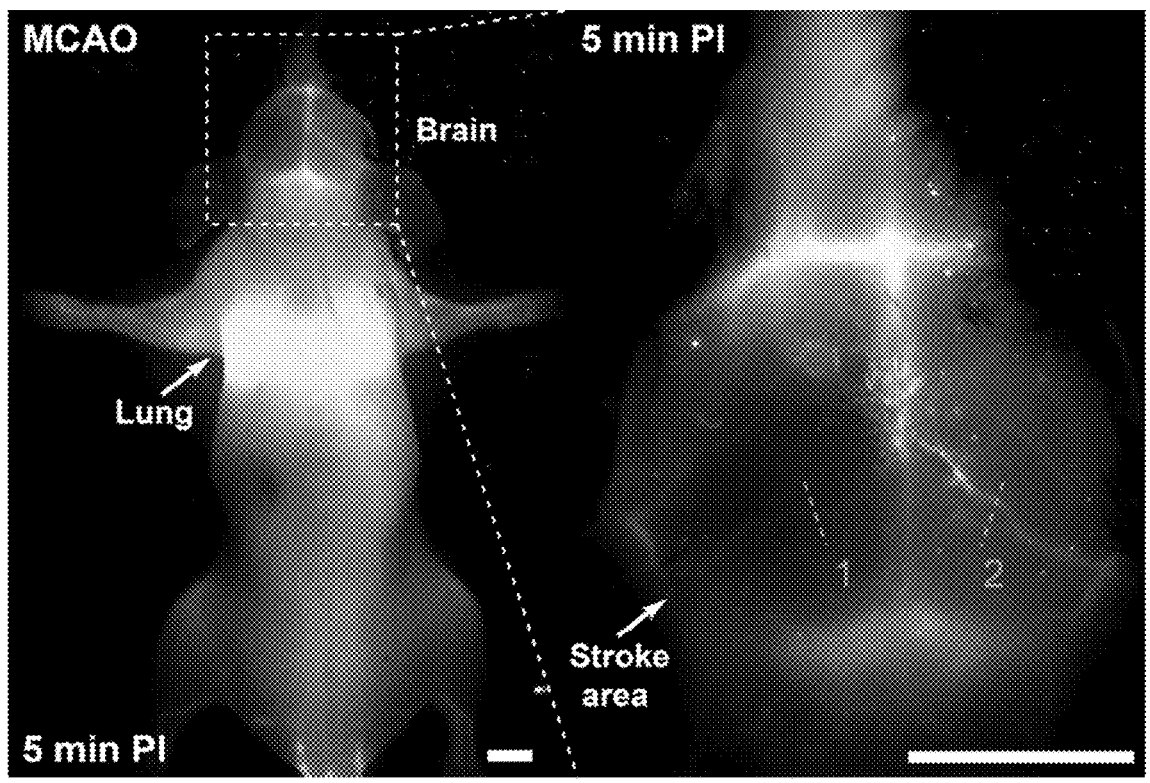
FIGS. 6A-6E illustrate unveiling the brain vascular structure of a MCAO mouse model and MSC response to brain inflammation in a MCAO mouse.
Figure 6B:
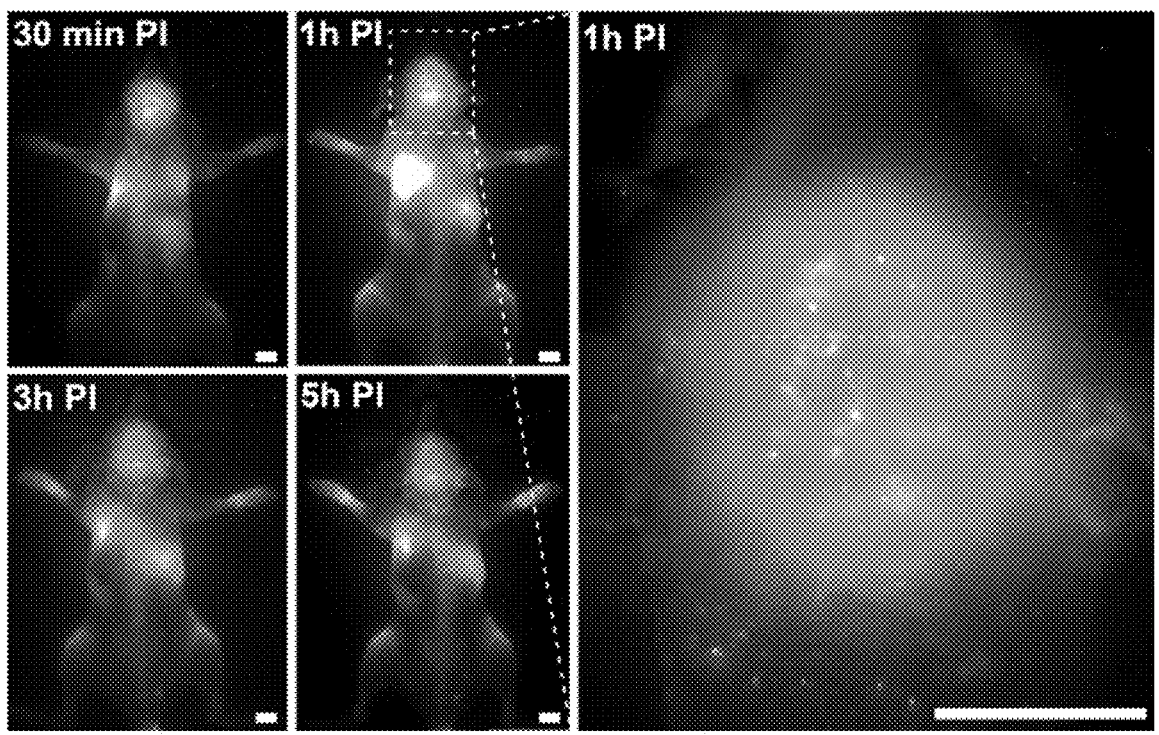

Ischemic stroke is one of the major causes of mortality in developed countries and the leading cause of long-term disability worldwide.(43) To investigate the in vivo cell migration and distribution in the treatment of ischemic stroke, a middle cerebral artery occlusion (MCAO) mouse model was provided, creating a stroke in the left cerebral hemisphere, according to the established protocol(44). The through-skull in vivo cerebrovascular fluorescence imaging of MCAO mice was carried out after intravenous administration of CelTrac1000-labeled MSCs. At 5-min post-MSC injection, the left hemisphere of the brain with the MCAO showed disrupted vascular structure, while the intact right hemisphere exhibited healthy vascular structure co-localized with the presence of labeled MSCs in the blood flow (FIG. 6A). At 30-min post-MSC injection, apparent migration of the MSCs to the stroke site of the left cerebral hemisphere was discovered. The MSCs were distributed across the whole brain in both the left and right hemispheres 1 h post cell administration (FIG. 6B). Cerebral ischemia is known to induce dramatic activation and release of various cytokines, chemokines and adhesion molecules.(45, 46) The inflammatory mediators released in the ischemia area can modulate the permeability of the blood brain barrier (BBB).(47) As a result, the dispersed MSCs across the whole-brain can be attributed to the enhanced BBB permeability and intense inflammatory reaction caused by the stroke.

Figure 6C:
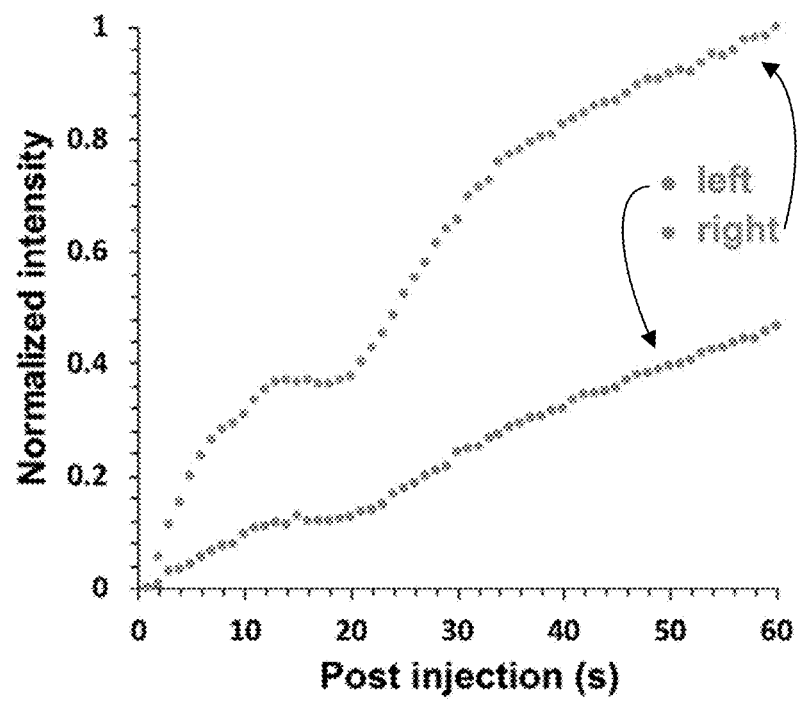
Figure 6D:
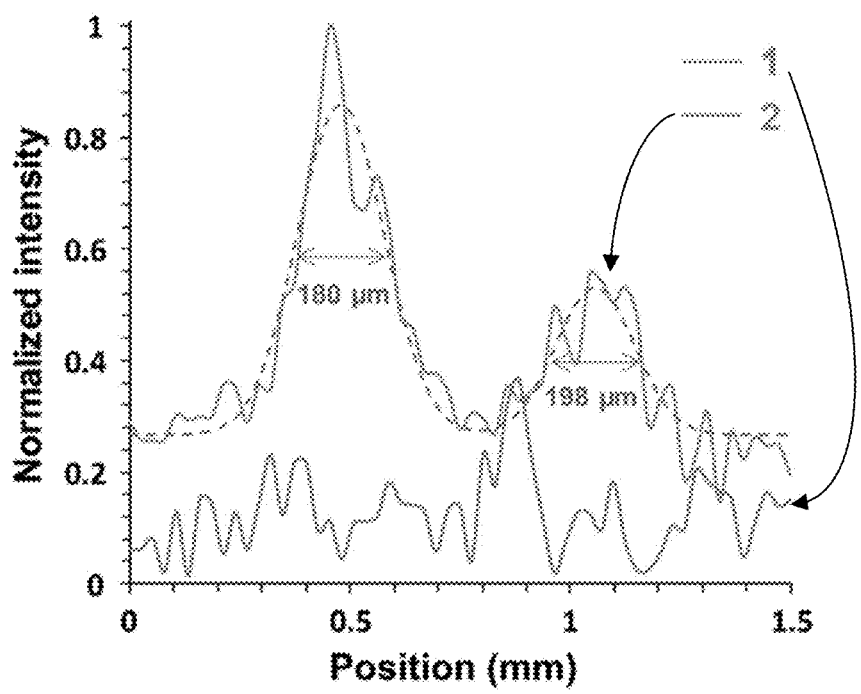
Figure 6E:
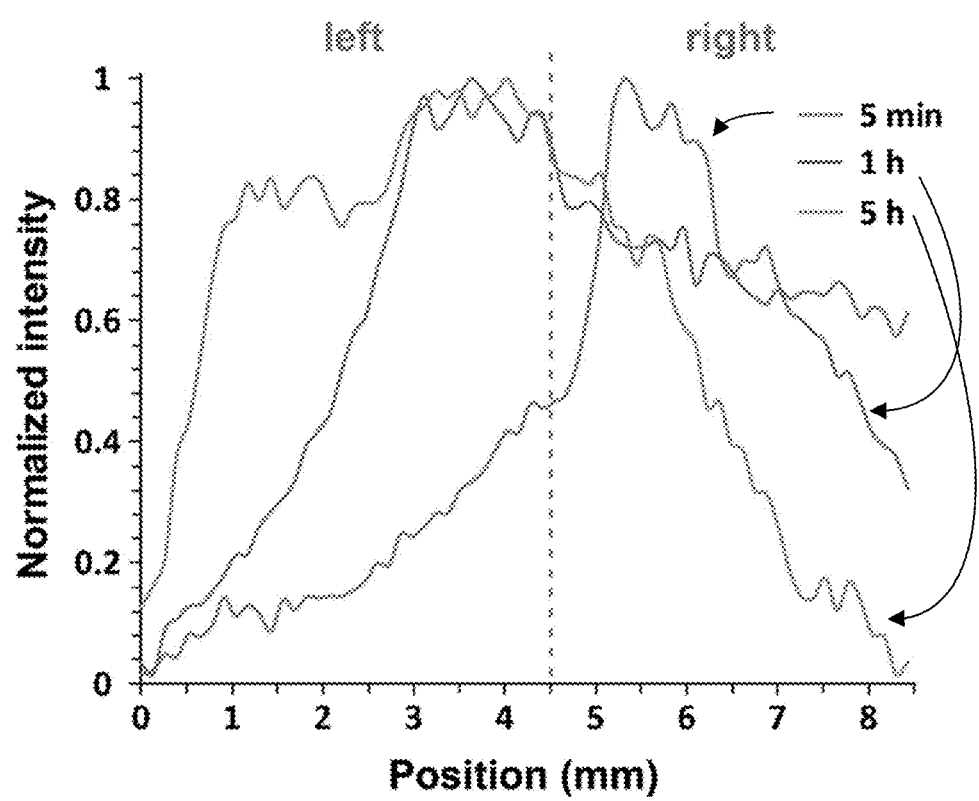

The dynamic fluorescence intensity changes in the left and right hemispheres of the MCAO mice were further quantitatively evaluated. The maxima of fluorescence cross-sectional intensities of the blood vessels from both hemispheres gradually increased in the first 60 s post-MSC injection due to the enrichment of the MSCs within brain vessels (FIG. 6C). In addition, the fluorescent signal of blood vessels in the right hemisphere showed much higher intensities as compared to those in the left hemisphere because the blockage of vessels constrained the blood flow at the stroke site. The cross-sectional NIR-II fluorescent intensity profile of line 2 in FIG. 6A showed a full-width half-maximum (FWHM) of 180 and 198 μm (FIG. 6D), indicating the ultrahigh imaging sensitivity of the labeled MSCs. Quantification of the cross-sectional NIR-II fluorescent intensity profile across the left and right hemispheres (the white line in the magnified brain image in FIG. 6E) can provide more details of the dynamic process of MSC migration in the brain. It suggests that the fluorescence intensity in the right hemisphere was much higher than that in the left hemisphere 5 min post-MSC injection, due to the higher concentration of MSCs in normal blood vessels compared to the blocked ones. Over time, the fluorescent intensity in the right hemisphere gradually decreased while the left hemisphere increased at 5 h post-injection. This phenomenon can be caused by the gradually decreasing concentration of MSCs in normal blood vessels, while the homing of MSCs at the stroke site became more and more significant due to enhanced BBB permeability and the triggered inflammation.

As a result, our approach provides a feasible and ultrasensitive technique to reveal the details of MSC migration and distribution in different disease models, which are hardly observed with conventional imaging methods. This opens a new avenue to facilitate and assist clinicians in providing a more precise treatment and outcome assessment when applied in stem cell therapy.

Discussion

In summary, a facile stem cell labeling and in vivo tracking technique has been realized to unveil the homing and migration of stem cells upon transplantation in mice models of various diseases. The single molecular tracker scales well for translational research and applications with simple synthesis and easily controlled quality. CelTrac1000 has shown its robust cell labeling and tracking capability on both stem cell-derived endothelial cells and primary mesenchymal stem cells, with low cellular toxicity and minimal effects on cell functions. Taking advantage of the merits of NIR-II fluorescence imaging, the present example successfully demonstrates that the single molecular NIR-II tracker can visualize the migration trajectory of single-cell clusters in the circulatory system with high sensitivity and temporal/spatial resolution. More importantly, the MSC distribution and migration have been imaged, analyzed and compared in both healthy and ALI, MI, and MCAO mice models in detail. This can help correlate critical biomedical information, such as stem cell dosing and engraftment and their relationships with efficacy, in stem cell therapies, providing more accurate therapeutic treatment and outcomes. Overall, this approach can provide researchers and clinicians a promising stem cell tracking approach to promote the translational potential of stem cell-based therapies in the near future.

Materials and Methods

Synthesis and Characterization of CelTrac1000

The water-soluble organic NIR-II dye, CH-4T, was synthesized as reported(35). HSA was conjugated with a Tat peptide through a two-step EDC/NHS coupling reaction in 10×PBS buffer. In brief, Tat peptide (RKKRRQRRRC, SEQ ID NO: 1) trifluoroacetic acid salt from GenicBio, China) (43.4 mg) was dissolved in 0.5 mL of dry DMSO with 89.2 mg EDC and 7.14 mg NHS for 1.5 h at room temperature. The activated Tat peptide was then mixed with 100 mg HSA (dissolved in 2 mL of 10×PBS). After reacting overnight at room temperature, the obtained Tat-HSA molecules were purified with an Amicon Ultra-5 mL 10 k to eliminate the excess free Tat peptides, EDC and NHS. To prepare 0.2 mL of 1 mM CelTrac1000 solutions, the obtained Tat-HSA (13.6 mg) and CH-4T (0.28 mg) were mixed in 1×PBS buffer (0.2 mL). The mixture was sealed in a 1.5 mL sterilized centrifuge tube and put into a bath sonicator for 30 min to afford CelTrac1000. The stock solution was then stored at 4° C. for further use.

Characterization of CelTrac1000

The molecular weights of HSA, Tat-HSA, and CelTrac1000 (Tat-HSA/CH-4T) were measured by matrix-assisted laser desorption/ionization time of flight mass spectrometry (MALDI-TOF MS). The absorption spectrum of CelTrac1000 in water was recorded on an ultraviolet-visible-NIR Cary 6000i spectrophotometer. The NIR-II fluorescence spectrum was recorded on a customized spectroscope, with excitation at 808 nm and a power output of ~160 mW. The excitation laser was filtered with a combination of an 850/1,000/1,100/1,200/1,300/1,350/1,400 nm long-pass filters (Thorlabs). The sample was loaded into a 1 cm path-length cuvette and the signal was filtered through a 910 nm long-pass filter (Thorlabs) to reject the incident excitation laser light. The emitted signal was recorded on a spectrometer (IsoPlane SCT-320) coupled to a liquid nitrogen-cooled InGaAs detector array (Princeton Instruments, NIRvana TE 640). Upon acquisition of the raw data, a correction file was applied to correct the variable InGaAs quantum efficiency as a function of detection wavelength, as well as the variable 910 nm long-pass filter extinction features across the NIR-II spectral region. A series of absorption and emission profiles of CelTrac1000 solutions were measured at probe concentrations of 0, 1.5625, 3.125, 6.25, 12.5, 25, and 50 µM.

NIR-II Imaging

Mice tail vein was infused with a venous catheter for IV injection of labeled cells or probes. All NIR-II images were collected on a 640×512 pixels two-dimensional InGaAs array (Princeton Instruments, NIRvana TE 640). The excitation laser was an 808 nm laser diode at a power density of ~140 mW cm$^{-2}$. Emission was typically collected with 1000, 1100 nm LP filter (Thorlabs). A prime lens (50 mm or 75 mm, Edmund Optics) was used to obtain magnifications ranging from 1× (whole-body) to 2.5× (high magnification) magnification by changing the relative position of the camera, lens, and animals. A binning of 1 and the variable exposure time was used for the InGaAs camera (640×512 pixels) to capture images in the NIR-II window. Images were processed with ImageJ (NIH).

NIR-II Fluorescent Microscopy Imaging

A Nikon ECLIPSE Ni fluorescent microscope with an InGaAs camera (Princeton Instruments, NIRvana TE 640), 785 nm, 100 mW/cm$^2$ laser excitation, 1000 nm long-pass filter (Thorlabs), 800 nm short-pass filter (Thorlabs) and 805 nm cut-on long pass dichroic mirror (Thorlabs) was used for NIR-II fluorescent microscopy imaging.

Study of Cellular Uptake and Leakage of CelTrac1000

Mouse mesenchymal stem cells (MSCs) and human-induced pluripotent stem cell-derived endothelial cells (iPSC-ECs) were seeded in 6-well plates individually at a density of 0.5 million cells per well (n=4 each). When the cells reached 80% confluence, 50 µM of CelTrac1000 in 2 mL of culture medium was added into each well. At designated time intervals (0, 0.5, 1, 2, 4, 6, 8, 12, 24, and 48 h), medium (100 µL) was collected from each well for further analysis of uptake efficiency through fluorescence measurement. At 48 h, each well was washed with PBS buffer, and 3 mL of fresh culture medium was added. Upon addition of the fresh medium, medium (100 µL) was then collected from each well at 0, 0.5, 1, 2, 4, 6, 12, 24, and 48 h for further analysis of leakage from cells. After washing, lipopolysaccharide (LPS) was diluted in 3 mL of medium (10 µg/mL) and added into each well for culture. After 0, 0.5, 1, 2, 4, 6 h, medium (100 µL) was collected from each well. The LPS medium was then discarded and 3 mL of fresh medium was added into each well, followed by a collection of 100 µL of the medium at 12, 24, and 48 h. The collected samples were analyzed to obtain fluorescence intensities for analysis of probe leakage from cells after treatment with LPS. The calculation formulas are in the supporting material.

Cytotoxicity of CelTrac1000

The metabolic activity of MSCs and ECs was evaluated by CellTiter 96® AQueous One Solution Cell Proliferation Assay (Promega) individually. MSCs and ECs were seeded in 96-well plates at 2×10$^4$ cells/mL. After 24 h incubation, the medium was replaced by CelTrac1000 solution at concentrations of 200, 100, 50, 25, 12.5, 6.25, 3.125, 1.5625 and 0.78125 µM, and the cells were then incubated for 48 h. The cells were washed twice by 1×PBS buffer, followed by addition of a mixture of 20 µL CellTiter 96® Aqueous reagent and 100 µL culture medium into each well. After further incubation for 1.5 h, the absorbance was recorded by a microplate reader at 490 nm (n=6 in each loading concentration). The cell viability was expressed as the ratio of absorbance from the cells incubated with CelTrac1000 to that of the cells incubated with culture medium only.

Effect of CelTrac1000 on Gene Expression of iPSC-EC and MSC

The cellular responses of CelTrac1000 treatment on the transcriptional levels of iPSC-ECs were measured by the real-time quantitative PCR (RT-qPCR). First, RNA was extracted using the RNeasy Mini Kit (Qiagen). All the RNAs used in this study were A260/280=1.9-2.1. Then 500 ng cDNA was synthesized via reverse transcription using the iScript cDNA Synthesis Kit (Bio-Rad). The qPCR was performed with the TaqMan gene expression assay, and the mRNA expression levels of CDH5, KDR, PECAM, NRG1, NOS3, and ICAM1 were examined. For MSCs, the mRNA expression levels of CD29, CD44, CD105, Sca-1 were analyzed. The final results were demonstrated as the relative expressions to the control group (N=3 in each group).

Long-Term Cell Tracking

MSCs and ECs were individually cultured in 6-well plates to achieve 80% confluence. After medium removal and washing with 1×PBS buffer, 50 µM of CelTrac1000 in culture medium was then added to the wells. After overnight incubation at 37° C., the cell monolayers were washed twice with 1×PBS buffer and cultured in fresh medium for 7, 14, 21, and 30 days, respectively. After designated time intervals, the NIR-II fluorescence images of cells were recorded upon excitation at 785 nm with a 1000 nm long-pass filter. To further investigate the detection limit of labelled cells in in vivo studies, different amounts of CelTrac1000-labelled ECs (250,000, 125,000, 62,500, 31,250, 15,625, 7,812, 3,906, 1,953, 976) were subcutaneously injected on the back of nude mice (n=4). The fluorescence images of these 9 spots were then recorded at designated time intervals (0, 7, 14, 21, 30 days) by a customized NIR-II small animal imaging facility upon excitation at 808 nm with a 1000 nm long-pass filter. The skin tissues were collected on day 30 for histological analysis.

Animal Handling

All animal experiments were approved by Stanford University's Administrative Panel on Laboratory Animal Care. Eight-week-old female C57BL/6 mice and BALB/c nude mice were purchased from Charles River for imaging studies and housed at the Research Animal Facility of Stanford University.

In Vivo Angiogenesis Assay.

The directed in vivo angiogenesis assay (DIVAA) was conducted to visualize the process of angiogenesis in nude mice (n=4). iPSC-ECs were first labeled by 50 µM of CelTrac1000 in culture medium at 37° C. for 12 h, followed by trypsinization to collect the cell suspensions. A semi-closed silicone strength (sealed top and open bottom, 5 mm in diameter) was filled with labeled iPSC-ECs and Matrigel. Two silicone angioreactors were separately loaded with different cell numbers (0.5 million and 1 million). The angioreactors were then subcutaneously implanted at both sides of the lower back of nude mice. The mice were imaged under a customized NIR-II small animal imaging facility upon excitation at 808 nm with an 1100 nm long-pass filter at designated time intervals. After 1 and 7 months, the mice were sacrificed to collect the angioreactors for ex vivo evaluation of the regenerative effect of transplanted iPSC-ECs.

Surgical Procedures of Animal Models

Female C57BL/6 mice (n=4 each group) were used to create acute lung injury (ALI), myocardial infarction (MI), and middle cerebral artery occlusion (MCAO) models for imaging studies, following the procedures reported in the literature(48-50). In brief, ALI was induced by giving LPS in 1×PBS solution through intratracheal instillation at a dose of 2 mg/kg. The LPS-treated mice were housed for another 24 h before imaging studies. The sub-acute MI model was achieved via coronary ligation for 60 minutes, followed by reperfusion. In the surgery, a polypropylene suture was passed from the left fringe of the pulmonary infundibulum to the lower right of the left auricle for ligation. The mice were then housed for 4 days before stem cell therapy and imaging. The silicon-tripped intraluminal thread occlusion method was employed to establish the MCAO mouse model. An 11 mm silicone-coated nylon thread was introduced into the left common carotid artery of the mouse and directed into the internal carotid artery until it obstructed blood flow to the middle cerebral artery. After 60 minutes, the filament was withdrawn and wounds were sutured. The mice were then housed for another 24 h before imaging studies. All the surgical procedures were performed when the mice were under anesthesia. H&E staining of organs was performed to confirm the success of disease models after imaging studies.

In Vivo Dynamic Tracking of MSCs in the Circulation System of Mice

Before imaging studies, the hair of C57BL/6 mice was shaved using a depilatory gel. During imaging processes, the mice (n=4) were placed on an imaging stage connected with an electric heating pad to maintain a consistent temperature. Mouse MSCs isolated from C57BL/6 mice were expanded and incubated with 50 μM of CelTrac1000 in culture medium at 37° C. for 12 h, followed by trypsinization to collect the cell suspensions. The labeled MSCs (2 million) were suspended in 1×PBS (200 μL) and injected into the healthy mouse through the tail vein. Real-time NIR-II fluorescent images were recorded by a customized NIR-II small animal imaging facility upon excitation at 808 nm with a 1000 nm or 1100 nm long-pass filter with an exposure time of 50 ms, 100 ms or 200 ms. The real-time monitoring of the injected MSCs in blood vessels, movement of lung lobes during inspiration and expiration, and heartbeat behavior were investigated to reveal the dynamic behavior of MSCs in the circulation system.

In Vivo Cell Tracking in Disease Models

MSCs were first incubated with 50 μM of CelTrac1000 in culture medium at 37° C. for 12 h, followed by trypsinization to collect the cell suspensions. The labeled MSCs (1 million) were suspended in 1×PBS (200 μL) and injected into the ALI/MI/MCAO mouse model through the tail vein. The fluorescent images of mice were then recorded at designated time intervals (0, 5 minutes, 1 h, 3 h, 6 h, 1 day and 3 days) by a customized NIR-II small animal imaging facility upon excitation at 808 nm with a 1000 nm long-pass filter (ALI/MI) or 1100 nm long-pass filter (MCAO). In the ALI model study, the same amount of labeled MSCs was intravenously injected into each healthy mouse for biodistribution comparison.

Histological Analyses of Engraftment of iPSC-ECs

The engraftment of iPSC-ECs in nude mice (n=4) skin tissues was investigated to evaluate their participation in angiogenesis. The mice were sacrificed at day 30 post iPSC-EC injection. The full-thickness skin tissues from the cell injection spots were collected and placed in an Optimal Cutting Temperature compound (Thermo Fisher Scientific, Hampton, NH, USA) on dry ice for embedding and freezing. The blocks were then cryo-sectioned into sections at 10 μm thickness for immunofluorescence staining processes. The slides were fixed in an ice-cold acetone/methanol mixture (50%/50%) and stained with primary anti-mouse CD144 antibody (MAB9381, 1:100, R&D Systems) and secondary donkey-anti-mouse Alexa Fluor® 594 (A21203, 1:200, Thermo Fisher Scientific), anti-human mitochondria antibody Alexa Fluor® 488 conjugate (MAB1273A4, 1:100, EMD Millipore), and DAPI.

Statistical Analyses

Data from different groups were analyzed by the student's t-test, and differences at the 95% confidence level (p<0.05) were considered to be statistically significant.

Mathematical Formulas and Calculations:

The calculation formulas of cellular uptake and leakage of CelTrac1000:

The cumulative amount of cellular uptake and leakage of CelTrac1000 MSCs and iPSC-ECs were calculated as follows:

Uptake:
first 24 h $$P_{n(uptake\ in\ cell)}\% = \frac{\text{Mol}_{n(in\ cell)}}{\text{Mol}_{(original)}} \times 100$$

$$= \frac{\text{Mol}_{n(in\ cell)} - \left[\text{Mol}_{n(in\ present\ medium)} + \sum_{i=1}^{n-1}\text{Mol}_{n-1(in\ taken\ out\ medium)}\right]}{\text{Mol}_{(original)}} \times 100$$

$$= 100 - \frac{\left[\text{Mol}_{n(in\ present\ medium)} + \sum_{i=1}^{n-1}\text{Mol}_{n-1(in\ taken\ out\ medium)}\right]}{\text{Mol}_{(original)}} \times 100$$

$$= 100 - \frac{\left\{[2\ \text{mL} - 0.1\ \text{mL}(n-1)]C_{n(in\ present\ medium)} + \sum_{i=1}^{n-1}\text{Mol}_{n-1(in\ taken\ out\ medium)}\right\}}{\text{Mol}_{(original)}} \times 100$$

48 h $$P_{10(48h\ uptake\ in\ cell)}\% =$$

$$100 - \frac{\left\{2\ \text{mL} \times C_{n(in\ present\ medium)} + \sum_{i=1}^{n-1}\text{Mol}_{n-1(in\ taken\ out\ medium)}\right\}}{\text{Mol}_{(original)}} \times 100$$

Where:

$$\sum_{i=1}^{n-1}\text{Mol}_{n-1(in\ taken\ out\ medium)}] =$$

$$0.1\ \text{mL} \times C_1 + 0.1\ \text{mL} \times C_2 + \ldots\ 0.1\ \text{mL} \times C_{(n-1)}$$

where P is the cumulative percentage of 4T/HSA-Tat in EC or MSC compare with the original, $\text{Mol}_{n\ (in\ cell)}$ is the $n^{th}$ mole amount of probe in cells, $\text{Mol}_{(original)}$ is the original mole amount of probe which was put into mediums, $\text{Mol}_{n(in\ present\ medium)}$ is the $n^{th}$ probe (mole amount) in present medium, $\text{Mol}_{n-1(in\ taken\ out\ medium)}$ is the $(n-1)^{th}$ mole amount of the probe in taken out medium. $C_n$ is the probe concentration of the $n^{th}$ taken out mediums (μmol/L).

Release:

$$P_{m\,(in\ cell\ after\ release)}\% =$$

$$\frac{Mol_{(uptake\ in\ cell\ after\ 48\ h)} - Mol_{(total\ release\ in\ medium)}}{Mol_{(original)}} \times 100 =$$

$$\frac{Mol_{(uptake\ in\ cell\ after\ 48\ h)} - \left[Mol_{m(in\ present\ medium)} + \sum_{i=1}^{m-1} Mol_{m-1(in\ taken\ out\ medium)}\right]}{Mol_{(original)}} \times 100 =$$

$$P_{(uptake\ in\ cell\ after\ 48\ h)} - \frac{\left[Mol_{m(in\ present\ medium)} + \sum_{i=1}^{m-1} Mol_{m-1(in\ taken\ out\ medium)}\right]}{Mol_{(original)}} \times 100 =$$

$$P_{(uptake\ in\ cell\ after\ 48\ h)} - \frac{\left\{[3\ mL - 0.1\ mL(m-1)]C_{m(in\ present\ medium)} + \sum_{i=1}^{m-1} Mol_{m-1(in\ taken\ out\ medium)}\right\}}{Mol_{(original)}} \times 100$$

Where:

$$\sum_{i=1}^{m-1} Mol_{m-1(in\ taken\ out\ medium)}] =$$

$$0.1\ mL \times C_1 + 0.1\ mL \times C_2 + \ldots 0.1\ mL \times C_{(m-1)}$$

where P is the cumulative percentage of 4T/HSA-Tat in EC or MSC compare with the original, $\text{Mol}_{m(uptake\ in\ cell\ after\ 48\ h)}$ is the $m^{th}$ mole amount of probe in cells, $\text{Mol}_{(original)}$ is the original mole amount of probe which was put into mediums, $\text{Mol}_{m(in\ present\ medium)}$ is the $m^{th}$ probe (mole amount) in present medium, $\text{Mol}_{m-1(in\ taken\ out\ medium)}$ is the $(m-1)^{th}$ mole amount of the probe in taken out medium. $C_m$ is the probe concentration of the $m^{th}$ taken out mediums (μmol/L).

Release with IPS Treated:

$$P_{l\,(in\ cell\ with\ IPS)}\% = \frac{Mol_{(in\ cell\ after\ 48\ h\ release)} - Mol_{(total\ release\ in\ medium)}}{Mol_{(original)}} \times 100 =$$

$$\frac{Mol_{(in\ cell\ after\ 48\ h\ release)} - \left[Mol_{l(in\ present\ medium)} + \sum_{i=1}^{l-1} Mol_{l-1(in\ taken\ out\ medium)}\right]}{Mol_{(original)}} \times 100 =$$

$$P_{(in\ cell\ after\ 48\ h\ release)} - \frac{\left[Mol_{l(in\ present\ medium)} + \sum_{i=1}^{l-1} Mol_{l-1(in\ taken\ out\ medium)}\right]}{Mol_{(original)}} \times 100 =$$

$$P_{(in\ cell\ after\ 48\ h\ release)} - \frac{\left\{[3\ mL - 0.1\ mL(l-1)]C_{l(in\ present\ medium)} + \sum_{i=1}^{l-1} Mol_{l-1(in\ taken\ out\ medium)}\right\}}{Mol_{(original)}} \times 100$$

Where:

$$\sum_{i=1}^{l-1} Mol_{l-1(in\ taken\ out\ medium)}] =$$

$$0.1\ mL \times C_1 + 0.1\ mL \times C_2 + \ldots 0.1\ mL \times C_{(l-1)}$$

where P is the cumulative percentage of 4T/HSA-Tat in EC or MSC compare with the original, $\text{Mol}_{l(in\ cell\ after\ 48\ h\ release)}$ is the $l^{th}$ mole amount of probe in cells, $\text{Mol}_{(original)}$ is the original mole amount of probe which was put into mediums, $\text{Mol}_{l(in\ present\ medium)}$ is the $l^{th}$ probe (mole amount) in present medium, $\text{Mol}_{l-1(in\ taken\ out\ medium)}$ is the $(l-1)^{th}$ mole amount of the probe in taken out medium. $C_l$ is the probe concentration of the $l^{th}$ taken out mediums (μmol/L).

$$P_{r\,(in\ cell\ after\ 6\ h\ IPS)}\% = \frac{Mol_{(in\ cell\ after\ 6\ h\ IPS)} - Mol_{(total\ release\ in\ medium)}}{Mol_{(original)}} \times 100 =$$

$$\frac{Mol_{(in\ cell\ after\ 6\ h\ IPS)} - \left[Mol_{r(in\ present\ medium)} + \sum_{i=1}^{r-1} Mol_{r-1(in\ taken\ out\ medium)}\right]}{Mol_{(original)}} \times 100 =$$

$$P_{(in\ cell\ after\ 6\ h\ IPS)} - \frac{\left[Mol_{r(in\ present\ medium)} + \sum_{i=1}^{r-1} Mol_{r-1(in\ taken\ out\ medium)}\right]}{Mol_{(original)}} \times$$

$$100 = P_{(in\ cell\ after\ 6\ h\ IPS)} - \frac{\left\{[3\ mL - 0.1\ mL(r-1)]C_{r(in\ present\ medium)} + \sum_{i=1}^{r-1} Mol_{r-1(in\ taken\ out\ medium)}\right\}}{Mol_{(original)}} \times 100$$

Where:

$$\sum_{i=1}^{r-1} Mol_{r-1(in\ taken\ out\ medium)}] =$$

$$0.1\ mL \times C_1 + 0.1\ mL \times C_2 + \ldots 0.1\ mL \times C_{(r-1)}$$

where P is the cumulative percentage of 4T/HSA-Tat in EC or MSC compare with the original, $\text{Mol}_{r(in\ cell\ after\ 6\ h\ IPS)}$ is the $r^{th}$ mole amount of probe in cells, $\text{Mol}_{(original)}$ is the original mole amount of probe which was put into mediums, $\text{Mol}_{r(in\ present\ medium)}$ is the $r^{th}$ probe (mole amount) in present medium, $\text{Mol}_{r-1(in\ taken\ out\ medium)}$ is the $(r-1)^{th}$ mole amount of the probe in taken out medium. $C_r$ is the probe concentration of the $r^{th}$ taken out mediums (μmol/L).

REFERENCES

1. G. Chamberlain, J. Fox, B. Ashton, J. Middleton, Concise Review: Mesenchymal stem cells: their phenotype, differentiation capacity, immunological features, and potential for homin. *Stem Cells* 25, 2739-2749 (2007).
2. H. Wang, F. Cao, A. De, Y. Cao, C. Contag, S. S. Gambhir, J. C. Wu, X. Chen, Trafficking mesenchymal stem cell engraftment and differentiation in tumor-bearing mice by bioluminescence imaging. *Stem Cells* 27, 1548-1558 (2009).
3. I. L. Weissman, Stem cells: units of development, review units of regeneration, and units in evolution. *Cell* 100, 157-168 (2000).

4. I. J. Fox, G. Q. Daley, S. A. Goldman, J. Huard, T. J. Kamp, M. Trucco, Stem cell therapy. Use of differentiated pluripotent stem cells as replacement therapy for treating disease. *Science* 345, 1247391 (2014).
5. A. Trounson, C. McDonald, Stem cell therapies in clinical trials: progress and challenges. *Cell Stem Cell* 17, 11-22 (2015).
6. V. Volarevic, B. Ljujic, P. Stojkovic, A. Lukic, N. Arsenijevic, M. Stojkovic, Human stem cell research and regenerative medicine—present and future. *Br. Med. Bull.* 99, 155-168 (2011).
7. V. Volarevic, B. S. Markovic, M. Gazdic, A. Volarevic, N. Jovicic, N. Arsenijevic, L. Armstrong, V. Djonov, M. Lako, M. Stojkovic, Ethical and safety issues of stem cell-based therapy. *Int. J. Med. Sci.* 15, 36-45 (2018).
8. P. J W, Tumour-educated macrophages promote tumour progression and metastasis. *Nat. Rev. Cancer* 4, 71-78 (2004).
9. S. M. Ridge, F. J. Sullivan, S. A. Glynn, Mesenchymal stem cells: key players in cancer progression. *Mol Cancer* 16, 31 (2017).
10. M. E. A. Becker A J, Till J E Cytological demonstration of the clonal nature of spleen colonies derived from transplanted mouse marrow cells. *Nature* 197, 452-454 (1963).
11. K. Schepers, T. B. Campbell, E. Passegue, Normal and leukemic stem cell niches: insights and therapeutic opportunities. *Cell Stem Cell* 16, 254-267 (2015).
12. X. Liang, Y. Ding, Y. Zhang, H. F. Tse, Q. Lian, Paracrine mechanisms of mesenchymal stem cell-based therapy: current status and perspectives. *Cell Transplant.* 23, 1045-1059 (2014).
13. J. A. Ankrum, J. F. Ong, J. M. Karp, Mesenchymal stem cells: immune evasive, not immune privileged. *Nat. Biotechnol.* 32, 252-260 (2014).
14. S. W. Lane, D. A. Williams, F. M. Watt, Modulating the stem cell niche for tissue regeneration. *Nat. Biotechnol.* 32, 795-803 (2014).
15. D. R. Pattabiraman, R. A. Weinberg, Tackling the cancer stem cells—what challenges do they pose? *Nat. Rev. Drug. Discov.* 13, 497-512 (2014).
16. G. J. Yoshida, H. Saya, Therapeutic strategies targeting cancer stem cells. *Cancer Sci.* 107, 5-11 (2016).
17. D. Cyranoski, Japan poised to allow 'reprogrammed' stem-cell therapy for damaged corneas. *Nature*, (2019).
18. T. Ng, Stem-cell therapy: what dose should we use? *Lancet* 364, 1935-1936 (2004).
19. M. F. Kircher, S. S. Gambhir, J. Grimm, Noninvasive cell-tracking methods. *Nat. Rev. Clin. Oncol.* 8, 677-688 (2011).
20. M. F. e. a. Kircher, In vivo high resolution three-dimensional imaging of antigen-specific cytotoxic T-lymphocyte trafficking to tumors. *Cancer Res.* 63, 6838-6846 (2003).
21. M. J. e. a. Pittet, In vivo imaging of T cell delivery to tumors after adoptive transfer therapy. *Proc. Natl Acad. Sci. USA* 104, 12457-12461 (2007).
22. S. J. Zhang, J. C. Wu, Comparison of imaging techniques for tracking cardiac stem cell therapy. *J. Nucl. Med.* 48, 1916-1919 (2007).
23. K. Hoshino, H. Q. Ly, J. V. Frangioni, R. J. Hajjar, In vivo tracking in cardiac stem cell-based therapy. *Prog. Cardiovasc. Dis.* 49, 414-420 (2007).
24. P. D. Z. Acton, R., Imaging reporter genes for cell tracking with PET and SPECT. *The Quarterly Journal of Nuclear Medicine and Molecular Imaging* 49, 349-360 (2005).
25. S. S. Yaghoubi, PET and SPECT Reporter Gene Imaging. *Molecular Imaging Probes for Cancer Research*, 373-415 (2012).
26. S. Luo, E. Zhang, Y. Su, T. Cheng, C. Shi, A review of NIR dyes in cancer targeting and imaging. *Biomaterials* 32, 7127-7138 (2011).
27. G. Hong, A. L. Antaris, H. Dai, Near-infrared fluorophores for biomedical imaging. *Nature Biomedical Engineering* 1, 0010 (2017).
28. Z. Hu, C. Fang, B. Li, Z. Zhang, C. Cao, M. Cai, S. Su, X. Sun, X. Shi, C. Li, T. Zhou, Y. Zhang, C. Chi, P. He, X. Xia, Y. Chen, S. S. Gambhir, Z. Cheng, J. Tian, First-in-human liver-tumour surgery guided by multispectral fluorescence imaging in the visible and near-infrared-I/II windows. *Nat Biomed Eng*, (2019).
29. C. Liang, C. Wang, Z. Liu, Stem Cell Labeling and Tracking with Nanoparticles. *Particle & Particle Systems Characterization* 30, 1006-1017 (2013).
30. J. D. K. K.-B. L. Aniruddh Solanki, Nanotechnology for regenerative medicine: nanomaterials for stem cell imaging. *Nanomedicine* 3, 567-578 (2008).
31. G. C. Chen, F. Tian, Y. Zhang, Y. J. Zhang, C. Y. Li, Q. B. Wang, Tracking of Transplanted Human Mesenchymal Stem Cells in Living Mice using Near-Infrared Ag-2 S Quantum Dots. *Adv. Funct. Mater.* 24, 2481-2488 (2014).
32. S. S. Chetty, S. Praneetha, K. Govarthanan, R. S. Verma, A. V. Murugan, Noninvasive Tracking and Regenerative Capabilities of Transplanted Human Umbilical Cord-Derived Mesenchymal Stem Cells Labeled with Semiconducting Nanocrystals in Liver-Injured Living Mice. *Acs Appl Mater Inter* 11, 8763-8778 (2019).
33. H. Wan, J. Y. Yue, S. J. Zhu, T. Uno, X. D. Zhang, Q. L. Yang, K. Yu, G. S. Hong, J. Y. Wang, L. L. Li, Z. R. Ma, H. P. Gao, Y. T. Zhong, J. Su, A. L. Antaris, Y. Xia, J. Luo, Y. Y. Liang, H. J. Dai, A bright organic NIR-II nanofluorophore for three-dimensional imaging into biological tissues. *Nat. Commun.* 9, (2018).
34. G. S. Hong, J. C. Lee, J. T. Robinson, U. Raaz, L. M. Xie, N. F. Huang, J. P. Cooke, H. J. Dai, Multifunctional in vivo vascular imaging using near-infrared II fluorescence. *Nat Med* 18, 1841 (2012).
35. A. L. Antaris, H. Chen, S. Diao, Z. Ma, Z. Zhang, S. Zhu, J. Wang, A. X. Lozano, Q. Fan, L. Chew, M. Zhu, K. Cheng, X. Hong, H. Dai, Z. Cheng, A high quantum yield molecule-protein complex fluorophore for near-infrared II imaging. *Nat Commun* 8, 15269 (2017).
36. K. M. Dupont, K. Sharma, H. Y. Stevens, J. D. Boerckel, A. J. Garcia, R. E. Guldberg, Human stem cell delivery for treatment of large segmental bone defects. *Proc Natl Acad Sci USA* 107, 3305-3310 (2010).
37. B. J. Muller-Borer, M. C. Collins, P. R. Gunst, W. E. Cascio, A. P. Kypson, Quantum dot labeling of mesenchymal stem cells. *J Nanobiotechnology* 5, 9 (2007).
38. Thermofisher, Cell Tracking. https://www.thermofisher.com/us/en/home/life-science/cell-analysis/cell-tracing-tracking-and-morphology/cell-tracking.html.
39. K. H. Nakayama, G. Hong, J. C. Lee, J. Patel, B. Edwards, T. S. Zaitseva, M. V. Paukshto, H. Dai, J. P. Cooke, Y. J. Woo, N. F. Huang, Aligned-Braided Nanofibrillar Scaffold with Endothelial Cells Enhances Arteriogenesis. *ACS Nano* 9, 6900-6908 (2015).
40. G. L. Liu, H. J. Lv, Y. L. An, X. X. Wei, X. M. Yi, H. M. Yi, Tracking of transplanted human umbilical cord-derived mesenchymal stem cells labeled with fluorescent probe in a mouse model of acute lung injury. *Int J Mol Med* 41, 2527-2534 (2018).

41. A. I. Caplan, Adult mesenchymal stem cells for tissue engineering versus regenerative medicine. 213, 341-347 (2007).
42. K. Suda, M. Tsuruta, J. Eom, C. Or, T. Mui, J. E. Jaw, Y. X. Li, N. Bai, J. Kim, J. Man, D. Ngan, J. Lee, S. Hansen, S. W. Lee, S. Tam, S. P. Man, S. Van Eeden, D. D. Sin, Acute Lung Injury Induces Cardiovascular Dysfunction Effects of IL-6 and Budesonide/Formoterol. *Am. J. Respir. Cell Mol. Biol.* 45, 510-516 (2011).
43. B. Ovbiagele, M. N. Nguyen-Huynh, Stroke Epidemiology: Advancing Our Understanding of Disease Mechanism and Therapy. *Neurotherapeutics* 8, 319 (2011).
44. R. Hata, G. Mies, C. Wiessner, K. Fritze, D. Hesselbarth, G. Brinker, K. A. Hossmann, A reproducible model of middle cerebral artery occlusion in mice: Hemodynamic, biochemical, and magnetic resonance imaging. *J Cerebr Blood F Met* 18, 367-375 (1998).
45. L. Pantoni, C. Sarti, D. Inzitari, Cytokines and Cell Adhesion Molecules in Cerebral Ischemia. *Arteriosclerosis, Thrombosis, and Vascular Biology* 18, 503-513 (1998).
46. G. del Zoppo, I. Ginis, J. M. Hallenbeck, C. Iadecola, X. Wang, G. Z. Feuerstein, Inflammation and Stroke: Putative Role for Cytokines, Adhesion Molecules and iNOS in Brain Response to Ischemia. *Brain Pathology* 10, 95-112 (2000).
47. K. E. Sandoval, K. A. Witt, Blood-brain barrier tight junction permeability and ischemic stroke. *Neurobiology of Disease* 32, 200-219 (2008).
48. C. B. Yuan, L. Tian, B. Yang, H. Y. Zhou, Isoalantolactone protects LPS-induced acute lung injury through Nrf2 activation. *Microb Pathogenesis* 123, 213-218 (2018).
49. D. J. Beard, D. D. McLeod, C. L. Logan, L. A. Murtha, M. S. Imtiaz, D. F. van Helden, N. J. Spratt, Intracranial pressure elevation reduces flow through collateral vessels and the penetrating arterioles they supply. A possible explanation for 'collateral failure' and infarct expansion after ischemic stroke. *J Cerebr Blood F Met* 35, 861-872 (2015).
50. J. F. Wang, H. B. Bo, X. Y. Meng, Y. Wu, Y. L. Bao, Y. X. Li, A simple and fast experimental model of myocardial infarction in the mouse. *Tex Heart I J* 33, 290-293 (2006).

wherein the probe emits detectable NIR-II fluorescence and wherein the molar ratio of the NIR-II dye molecule to carrier protein to CPP is from about 0.5-1.5 NIR-II dye molecule to 0.5-1.5 carrier protein to 0.5-1.5 CPP.

2. The NIR-II optical imaging probe of claim 1, wherein the carrier protein comprises a serum albumin protein.

3. The NIR-II optical imaging probe of claim 2, wherein the serum albumin protein is selected from human serum albumin (HSA) molecule and bovine serum albumin (BSA) molecule.

4. The NIR-II optical imaging probe of claim 1, wherein the CPP comprises trans-activator of transcription (Tat) peptide of HIV, or a derivative or segment thereof retaining cell membrane penetrating functionality.

5. The NIR-II optical imaging probe of claim 4, wherein the Tat peptide comprises a peptide sequence having at least 75% sequence identity with SEQ ID NO: 1.

6. The NIR-II optical imaging probe of claim 1, wherein the biocompatible NIR-II dye molecule is selected from the group consisting of: CH-4T, CH1055, carboxyl NIR-II dye molecules, NIR-II cyanine dye molecules, and combinations thereof.

7. The NIR-II optical imaging probe of claim 6, wherein the biocompatible NIR-II dye molecule is CH-4T.

8. The NIR-II optical imaging probe of claim 1, wherein the carrier protein is coupled to the CPP through a carbodiimide-mediated coupling reaction.

9. The NIR-II optical imaging probe of claim 1, wherein the molar ratio of the NIR-II dye molecule to carrier protein to CPP is about 1 NIR-II dye molecule to 1 carrier protein to 1 CPP.

10. A cell including at least one NIR-II optical imaging probe of claim 1.

11. The cell of claim 10, wherein the cell is selected from the group consisting of: a stem cell, a pluripotent cell, an immune cell, a donor cell, and a cancer cell.

12. The cell of claim 10, wherein the cell is a human stem cell.

13. A pharmaceutically acceptable imaging composition comprising:
a plurality of NIR-II optical imaging probes of claim 1 or a plurality of target cells, wherein at least a portion of

The invention claimed is:

1. An NIR-II optical imaging probe comprising:
a biocompatible NIR-II dye molecule coupled to an organic, biocompatible protein carrier complex, the protein carrier complex comprising a carrier protein coupled to a cell-penetrating peptide (CPP), the target cells each include one or more of the NIR-II optical imaging probes of claim 1; and
a pharmaceutically acceptable carrier.

14. The pharmaceutically acceptable imaging composition of claim 13, wherein the composition comprises a plurality of target cells, wherein at least a portion of the target cells each include one or more of the NIR-II optical imaging probes of claim 1 and wherein the cells are selected from the group consisting of: stem cells, immune cells, and donor cells.

15. An imaging kit comprising:
- the pharmaceutically acceptable imaging composition of claim 13, and
- instructions for administration of the pharmaceutically acceptable imaging composition to a patient and imaging of the patient.

* * * * *

SEQUENCE LISTING

<160> NUMBER OF SEQ ID NOS: 1

<210> SEQ ID NO 1
<211> LENGTH: 10
<212> TYPE: PRT
<213> ORGANISM: Artificial Sequence
<220> FEATURE:
<223> OTHER INFORMATION: synthetic varient of Tat peptide from Human
      Immunodeficiency Virus.

<400> SEQUENCE: 1

Arg Lys Lys Arg Arg Gln Arg Arg Arg Cys
1               5                   10